United States Patent
Purcell et al.

(10) Patent No.: US 12,064,332 B2
(45) Date of Patent: Aug. 20, 2024

(54) SYSTEMS AND METHODS FOR PROTECTING THE CEREBRAL VASCULATURE

(71) Applicant: Claret Medical, Inc., Santa Rosa, CA (US)

(72) Inventors: Cameron Paul Purcell, Santa Rosa, CA (US); Antony J. Fields, Santa Rosa, CA (US); Whittaker Ian Hamill, Petaluma, CA (US); Daniel Wayne Fifer, Windsor, CA (US); Philip Jon Haarstad, Chanhassen, MN (US); David John Blaeser, Brooklyn Park, MN (US)

(73) Assignee: Claret Medical, Inc., Santa Rosa, CA (US)

( * ) Notice: Subject to any disclaimer, the term of this patent is extended or adjusted under 35 U.S.C. 154(b) by 211 days.

(21) Appl. No.: 17/507,052

(22) Filed: Oct. 21, 2021

(65) Prior Publication Data
US 2022/0039936 A1    Feb. 10, 2022

Related U.S. Application Data

(63) Continuation of application No. 16/225,359, filed on Dec. 19, 2018, now Pat. No. 11,154,390.
(Continued)

(51) Int. Cl.
*A61F 2/01*    (2006.01)
*A61M 25/00*   (2006.01)
*A61M 25/01*   (2006.01)

(52) U.S. Cl.
CPC ............ *A61F 2/012* (2020.05); *A61F 2/0105* (2020.05); *A61F 2/014* (2020.05);
(Continued)

(58) Field of Classification Search
CPC ........ A61F 2/012; A61F 2/0105; A61F 2/014; A61F 2/011; A61F 2002/016;
(Continued)

(56) References Cited

U.S. PATENT DOCUMENTS

| 3,472,230 A | 10/1969 | Fogarty |
| 4,619,246 A | 10/1986 | Molgaard-Nielsen et al. |

(Continued)

FOREIGN PATENT DOCUMENTS

| DE | 10049812 A1 | 4/2002 |
| EP | 1400257 A2 | 3/2004 |

(Continued)

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).
(Continued)

*Primary Examiner* — Elizabeth Houston
*Assistant Examiner* — Lindsey Bachman
(74) *Attorney, Agent, or Firm* — Seager, Tufte & Wickhem LLP

(57) ABSTRACT

Vascular filters and deflectors and methods for filtering bodily fluids. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

17 Claims, 8 Drawing Sheets

Related U.S. Application Data

(60) Provisional application No. 62/607,801, filed on Dec. 19, 2017.

(52) U.S. Cl.
CPC ......... *A61M 25/0147* (2013.01); *A61F 2/011* (2020.05); *A61F 2002/016* (2013.01); *A61F 2002/018* (2013.01); *A61M 25/0068* (2013.01)

(58) Field of Classification Search
CPC ......... A61F 2002/018; A61M 25/0147; A61M 25/0068; A61B 17/221; A61B 2017/2212; A61B 2017/2215
See application file for complete search history.

(56) References Cited

U.S. PATENT DOCUMENTS

| | | |
|---|---|---|
| 4,630,609 A | 12/1986 | Chin |
| 4,650,466 A | 3/1987 | Luther |
| 4,706,671 A | 11/1987 | Weinrib |
| 4,723,549 A | 2/1988 | Wholey et al. |
| 4,873,978 A | 10/1989 | Ginsburg |
| 5,108,419 A | 4/1992 | Reger |
| 5,192,286 A | 3/1993 | Phan et al. |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel et al. |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates et al. |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel et al. |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika et al. |
| 6,336,934 B1 | 1/2002 | Gilson et al. |
| 6,336,116 B1 | 2/2002 | Brooks et al. |
| 6,361,545 B1 | 3/2002 | Macoviak et al. |
| 6,364,900 B1 | 4/2002 | Heuser |
| 6,371,970 B1 | 4/2002 | Khosravi |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson |
| 6,440,120 B1 | 8/2002 | Maahs |
| 6,454,799 B1 | 9/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,922,732 B2 | 3/2011 | Mazzocchi et al. |
| 7,918,859 B2 | 4/2011 | Katoh et al. |
| 7,976,562 B2 | 7/2011 | Bressler et al. |
| 7,998,104 B2 | 8/2011 | Chang |
| 8,002,790 B2 | 8/2011 | Brady et al. |

(56) References Cited

U.S. PATENT DOCUMENTS

| | | | |
|---|---|---|---|
| 8,021,351 B2 | 9/2011 | Boldenow et al. |
| 8,052,713 B2 | 11/2011 | Khosravi et al. |
| 8,092,483 B2 | 1/2012 | Galdonik et al. |
| 8,206,412 B2 | 6/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2* | 11/2014 | Fifer .................. A61F 2/012 |
| | | | 604/95.04 |
| 8,974,489 B2 | 3/2015 | Lashinski |
| 9,017,364 B2 | 4/2015 | Fifer et al. |
| 9,055,997 B2 | 6/2015 | Fifer et al. |
| 9,211,178 B2 | 12/2015 | Rothstein et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 | 2/2017 | Purcell et al. |
| 9,636,205 B2 | 5/2017 | Lee et al. |
| 9,943,395 B2 | 4/2018 | Fifer et al. |
| 9,980,805 B2 | 5/2018 | Fifer |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 6/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0182268 A1* | 7/2009 | Thielen ............. A61M 25/0138 |
| | | | 604/95.04 |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0185231 A1 | 7/2010 | Lashinski |
| 2010/0211095 A1 | 8/2010 | Carpenter |
| 2010/0228280 A1 | 9/2010 | Groothius et al. |
| 2010/0312268 A1 | 12/2010 | Belson |
| 2010/0324589 A1 | 12/2010 | Carpenter et al. |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0172915 A1 | 7/2012 | Fifer et al. |
| 2012/0172918 A1* | 7/2012 | Fifer ............... A61B 17/22031 |
| | | | 606/200 |
| 2012/0179033 A1* | 7/2012 | Merhi .................. A61F 2/013 |
| | | | 604/529 |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0226223 A1 | 8/2013 | Spenser |
| 2013/0231694 A1 | 9/2013 | Lashinski |
| 2013/0238010 A1 | 9/2013 | Johnson et al. |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0249567 A1 | 9/2014 | Adams et al. |
| 2014/0282379 A1 | 9/2014 | Bijani et al. |
| 2014/0330366 A1* | 11/2014 | Dehdashtian ......... A61F 2/2433 |
| | | | 623/2.11 |
| 2015/0039016 A1 | 2/2015 | Naor et al. |

(56) References Cited

U.S. PATENT DOCUMENTS

| | | | |
|---|---|---|---|
| 2015/0073533 A1 | 3/2015 | Kassab et al. | |
| 2015/0230910 A1 | 8/2015 | Lashinski et al. | |
| 2015/0335416 A1 | 11/2015 | Fifer et al. | |
| 2016/0058541 A1 | 3/2016 | Schotzko et al. | |
| 2016/0066880 A1 | 3/2016 | Stigall et al. | |
| 2016/0262864 A1 | 9/2016 | Von Mangoldt et al. | |
| 2016/0310255 A1* | 10/2016 | Purcell | A61F 2/013 |
| 2016/0317276 A1* | 11/2016 | Groh | A61F 2/013 |
| 2017/0042658 A1 | 2/2017 | Lee et al. | |
| 2017/0112609 A1 | 4/2017 | Purcell et al. | |
| 2017/0181834 A1 | 6/2017 | Fifer et al. | |
| 2017/0202657 A1 | 7/2017 | Lee et al. | |
| 2018/0177582 A1 | 6/2018 | Lashinski | |
| 2018/0235742 A1 | 8/2018 | Fields et al. | |

FOREIGN PATENT DOCUMENTS

| | | |
|---|---|---|
| EP | 1253871 B1 | 2/2007 |
| EP | 2303384 A2 | 4/2011 |
| EP | 2391303 A2 | 12/2011 |
| EP | 2480165 A2 | 8/2012 |
| EP | 2658476 A1 | 11/2013 |
| EP | 2387427 B1 | 8/2014 |
| EP | 2859864 A1 | 4/2015 |
| JP | 2003505216 A | 2/2003 |
| JP | 2003526451 A | 9/2003 |
| JP | 2003290231 A | 10/2003 |
| JP | 3535098 B2 | 6/2004 |
| JP | 2006500187 A | 1/2006 |
| JP | 2008511401 A | 4/2008 |
| JP | 2008515463 A | 5/2008 |
| JP | 2011525405 A | 9/2011 |
| WO | 9923976 A1 | 5/1999 |
| WO | 0021604 A1 | 4/2000 |
| WO | 0108743 A1 | 2/2001 |
| WO | 0167989 A2 | 9/2001 |
| WO | 2004026175 A1 | 4/2004 |
| WO | 2005118050 A2 | 12/2005 |
| WO | 2006026371 A1 | 3/2006 |
| WO | 2006076505 A2 | 7/2006 |
| WO | 2008033845 A2 | 3/2008 |
| WO | 2008100790 A2 | 8/2008 |
| WO | 2008113857 A2 | 9/2008 |
| WO | 2009032834 A1 | 3/2009 |
| WO | 2010081025 A1 | 7/2010 |
| WO | 2010083527 A2 | 7/2010 |
| WO | 2011017103 A2 | 10/2011 |
| WO | 2018156655 A1 | 8/2018 |

OTHER PUBLICATIONS

Internet Archive Wayback Machine; Fiber Innovative Technology: 4DG Fibers; downloaded from http:/web.archive.org/web/20011030070010/http://fitfibers.com/4DG_Fibers.htm (Archived Oct. 30, 2001; printed on Dec. 12, 2016).

Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

International Search Report and Written Opinion dated Mar. 22, 2019 for International Application No. PCT/US2018/066404.

Kelley et al; "Anatomy, Thorax, Aortic Arch," National Center for Biotechnology Information—NCBI—Bookshelf. Treasure Island, FL: StatPearls Publishing, 2020 [retrieved on Nov. 10, 2020], Retrieved from the internet:URL:https://www.ncbi.nlm.nih.gov/books/NBK499911/figure/article-17736.image.fl/?report=objectonly>, 3 pages, (Year:2020). Last Update: Aug. 11, 2021. downloaded Nov. 23, 2021.

Extended European Search Report dated May 19, 2023, for Application No. 23160441.4-1113.

* cited by examiner

SYSTEMS AND METHODS FOR PROTECTING THE CEREBRAL VASCULATURE

CROSS-REFERENCE TO RELATED APPLICATIONS

This application is a continuation of U.S. application Ser. No. 16/225,359, filed Dec. 19, 2018, which claims the benefit of priority under 35 U.S.C. § 119 to U.S. Provisional Application Ser. No. 62/607,801, filed Dec. 19, 2017, the entirety of which is incorporated herein by reference.

TECHNICAL FIELD

In general, the present disclosure relates to medical devices for filtering blood. And, more particularly, in certain embodiments, to a method and a system of filters and deflectors for protecting the cerebral arteries from emboli, debris and the like dislodged during an endovascular or cardiac procedure.

BACKGROUND

There are four arteries that carry oxygenated blood to the brain, i.e., the right and left vertebral arteries, and the right and left common carotid arteries. Various procedures conducted on the human body, e.g., transcatheter aortic valve replacement (TAVR), aortic valve valvuloplasty, carotid artery stenting, closure of the left atrial appendage, mitral valve annuloplasty, repair or replacement, can cause and/or dislodge materials (whether native or foreign), these dislodged bodies can travel into one or more of the cerebral arteries resulting in, inter alia, stroke. Moreover, atheromas along and within the aorta and aortic arch can be dislodged as the TAVR catheter is advanced toward the diseased aortic valve and subsequently withdrawn after implantation is completed. In addition, pieces of the catheter itself can be stripped away during delivery and implantation. These various forms of vascular debris, whether native or foreign, can then travel into one or more cerebral arteries, embolize and cause, inter alia, a stroke or strokes.

There exist devices for protecting one or more cerebral arteries by either collecting (filters) or deflecting (deflectors) debris. Single filters, such as those used during a carotid artery stenting are one such device.

Applicants have previously patented a dual filter embolic protection system that protects the right vertebral, and right and left common carotid arteries, see e.g., U.S. Pat. No. 9,492,264, the entirety of which is incorporated herein. Other attempts at deflecting debris from entering one or more cerebral arteries using a deflector placed in the aorta or aortic arch have also been disclosed. Of the known medical devices, delivery systems, and methods, each has certain advantages and disadvantages. There is an ongoing need to provide alternative medical devices and methods as well as alternative methods for manufacturing and using medical devices.

SUMMARY

Certain aspects of the present disclosure address debris, tissue, etc., that can be dislodged during an endovascular procedure, this debris can travel toward, into and embolize within the cerebral vasculature leading to stroke or ischemia in an artery occluded, partially or totally, by the clot. For example, during a transcatheter aortic valve replacement (TAVR), stenotic material around the valve can be dislodged during implantation of the artificial valve. Moreover, atheroma along and within the aorta and aortic arch can be dislodged as the TAVR catheter is advanced toward the diseased aortic valve and subsequently withdrawn after implantation is completed. In addition, pieces of the catheter itself can be stripped away during delivery and implantation. These various forms of vascular debris, whether native or foreign, can then travel into one or more cerebral arteries, embolize and cause a stroke, strokes or neurocognitive deficits, for example.

Certain aspects of the present disclosure are intended to address these potentially devastating cerebral events by providing a delivery system comprised of filters and/or deflectors and/or combinations thereof, to intercept this debris before it can enter any of the cerebral arteries.

Certain aspects of the present disclosure, and its various embodiments, can provide a compound system of filters and/or deflectors for collecting (and/or deflecting) debris in a manner such that all four cerebral arteries are protected.

Vascular filters and deflectors and methods for filtering bodily fluids are disclosed herein. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

In a first example, a method of inhibiting embolic material from entering cerebral vasculature may comprise positioning a guidewire through a right subclavian artery and into a left common carotid artery and tracking a distal portion of a first protection device over the guidewire. The distal portion of the first protection device may comprise a proximal sheath, a proximal self-expanding filter assembly radially within the proximal sheath, a distal sheath, and a distal self-expanding filter assembly radially within the distal sheath. The method may further comprise at least one of proximally retracting the proximal sheath and distally advancing the proximal self-expanding filter assembly to deploy the proximal self-expanding filter assembly from the proximal sheath in the innominate artery, steering the distal sheath into a left common carotid artery, at least one of proximally retracting the distal sheath and distally advancing the distal self-expanding filter assembly to deploy the distal self-expanding filter assembly from the distal sheath in the left common carotid artery, after deploying the proximal and distal self-expanding filter assemblies, withdrawing the proximal and distal sheaths, and tracking a distal portion of a second protection device from an incision in a femoral artery to an aortic arch. The distal portion of the second protection device may comprise an outer sheath, an inner tubular member radially within the outer sheath, and a self-expanding filter assembly radially within the outer sheath and coupled to the inner tubular member. The method may further comprise at least one of least one of proximally retracting the outer sheath and distally advancing the inner tubular member to deploy the self-expanding filter assembly from the outer sheath.

Alternatively or additionally to any of the examples above, in another example, an opening of the self-expanding filter assembly of the second protection device may be positioned in the aortic arch upstream of an ostium of a left subclavian artery.

Alternatively or additionally to any of the examples above, in another example, the opening may be a distally facing opening.

Alternatively or additionally to any of the examples above, in another example, the second protection device may further comprise a pigtail catheter radially inward of the inner tubular member.

Alternatively or additionally to any of the examples above, in another example, the method may further comprise after deploying self-expanding filter assembly of the second protection device, withdrawing the pigtail catheter.

Alternatively or additionally to any of the examples above, in another example, the method may further comprise performing an endovascular procedure, the deployed proximal and distal filter assemblies of the first protection device and the self-expanding filter assembly of the second protection device inhibiting embolic material from entering cerebral vasculature through the left vertebral artery, a right common carotid artery, a right vertebral artery and the left common carotid artery during the endovascular procedure.

Alternatively or additionally to any of the examples above, in another example, the method may further comprise after performing the endovascular procedure, withdrawing the proximal and distal filter assemblies of the first protection device and the self-expanding filter assembly of the second protection device.

Alternatively or additionally to any of the examples above, in another example, a procedural catheter for performing the endovascular procedure may be advanced through a lumen of the inner tubular member of the second protection device.

Alternatively or additionally to any of the examples above, in another example, an opening of the self-expanding filter assembly of the second protection device may be positioned in a left subclavian artery upstream of an ostium of a left vertebral artery.

Alternatively or additionally to any of the examples above, in another example, the opening may be a proximally facing opening.

In another example, a method of inhibiting embolic material from entering cerebral vasculature may comprise positioning a first guidewire through a right subclavian artery and into a left common carotid artery and tracking a distal portion of a first protection device over the guidewire. The distal portion of the first protection device may comprise a proximal sheath, a proximal self-expanding filter assembly radially within the proximal sheath, a distal sheath, and a distal self-expanding filter assembly radially within the distal sheath. The method may further comprise at least one of proximally retracting the proximal sheath and distally advancing the proximal self-expanding filter assembly to deploy the proximal self-expanding filter assembly from the proximal sheath in the innominate artery, steering the distal sheath into a left common carotid artery, at least one of proximally retracting the distal sheath and distally advancing the distal self-expanding filter assembly to deploy the distal self-expanding filter assembly from the distal sheath in the left common carotid artery, after deploying the proximal and distal self-expanding filter assemblies, withdrawing the proximal and distal sheaths, positioning a second guidewire through a femoral artery and into a left subclavian artery, and tracking a distal portion of a second protection device over the second guidewire. The distal portion of the second protection device may comprise an outer sheath, a catheter shaft radially within the outer sheath, and an inflatable balloon radially within the outer sheath and coupled to the catheter shaft. The method may further comprise at least one of least one of proximally retracting the outer sheath and distally advancing the catheter shaft to deploy the inflatable balloon from the outer sheath in the left subclavian artery and inflating the inflatable balloon.

Alternatively or additionally to any of the examples above, in another example, the method may further comprise performing an endovascular procedure, the deployed proximal and distal filter assemblies and inflatable balloon inhibiting embolic material from entering cerebral vasculature through the left vertebral artery, a right common carotid artery, a right vertebral artery and the left common carotid artery during the endovascular procedure.

Alternatively or additionally to any of the examples above, in another example, the method may further comprise after performing the endovascular procedure, withdrawing the proximal and distal filter assemblies and the inflatable balloon.

Alternatively or additionally to any of the examples above, in another example, a procedural catheter for performing the endovascular procedure may be advanced through a lumen of the outer sheath of the second protection device.

In another example, an embolic protection system for isolating the cerebral vasculature may comprise a first protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The system may further comprise a second protection device having a proximal portion configured to remain outside the body and a distal portion. The distal portion of the second protection device may comprise an outer sheath, an inner tubular member radially within the outer sheath, a self-expanding filter assembly radially within the outer sheath and coupled to the inner tubular member, and a pigtail catheter radially within the outer sheath.

Alternatively or additionally to any of the examples above, in another example, the proximal self-expanding filter assembly may include a distally facing opening.

Alternatively or additionally to any of the examples above, in another example, the distal self-expanding filter assembly may include a proximally facing opening.

Alternatively or additionally to any of the examples above, in another example, the self-expanding filter assembly of the second protection device may include a distally facing opening.

Alternatively or additionally to any of the examples above, in another example, the self-expanding filter assembly of the second protection device may include a proximally facing opening.

Alternatively or additionally to any of the examples above, in another example, the pigtail catheter may be radially within the self-expanding filter assembly of the second protection device.

In another example, an embolic protection system for isolating the cerebral vasculature may comprise a first protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The system may further comprise a second protection device having a proximal portion configured to remain outside the body and a distal portion. The distal portion of the second protection device may comprise an outer sheath, an inner tubular member radially within the outer sheath, a mechanism configured to occlude a flow of particulates, the mechanism within the outer sheath and coupled to the inner tubular member, and a pigtail catheter radially within the outer sheath.

Alternatively or additionally to any of the examples above, in another example, the mechanism may comprise a self-expanding filter assembly.

Alternatively or additionally to any of the examples above, in another example, the self-expanding filter assembly of the second protection device may include a distally facing opening.

Alternatively or additionally to any of the examples above, in another example, the self-expanding filter assembly of the second protection device may include a proximally facing opening.

Alternatively or additionally to any of the examples above, in another example, the mechanism may comprise an inflatable balloon.

Alternatively or additionally to any of the examples above, in another example, the pigtail catheter may be radially within the inner tubular member.

Alternatively or additionally to any of the examples above, in another example, the system may further comprise a filter wire coupled to the self-expanding filter assembly of the second protection device.

Alternatively or additionally to any of the examples above, in another example, each of the proximal self-expanding filter, the distal self-expanding filter, and the mechanism may be configured to be individually deployed.

Alternatively or additionally to any of the examples above, in another example, at least one of the first or second protection devices may be connected to an arterial pressure monitoring device.

Alternatively or additionally to any of the examples above, in another example, the inner tubular member may comprise a guidewire lumen.

Alternatively or additionally to any of the examples above, in another example, the proximal sheath may be articulatable.

Alternatively or additionally to any of the examples above, in another example, the distal sheath may be articulatable.

Alternatively or additionally to any of the examples above, in another example, the outer sheath may be articulatable.

Alternatively or additionally to any of the examples above, in another example, the proximal self-expanding filter assembly may include a distally facing opening.

Alternatively or additionally to any of the examples above, in another example, the distal self-expanding filter assembly may include a proximally facing opening.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1A:
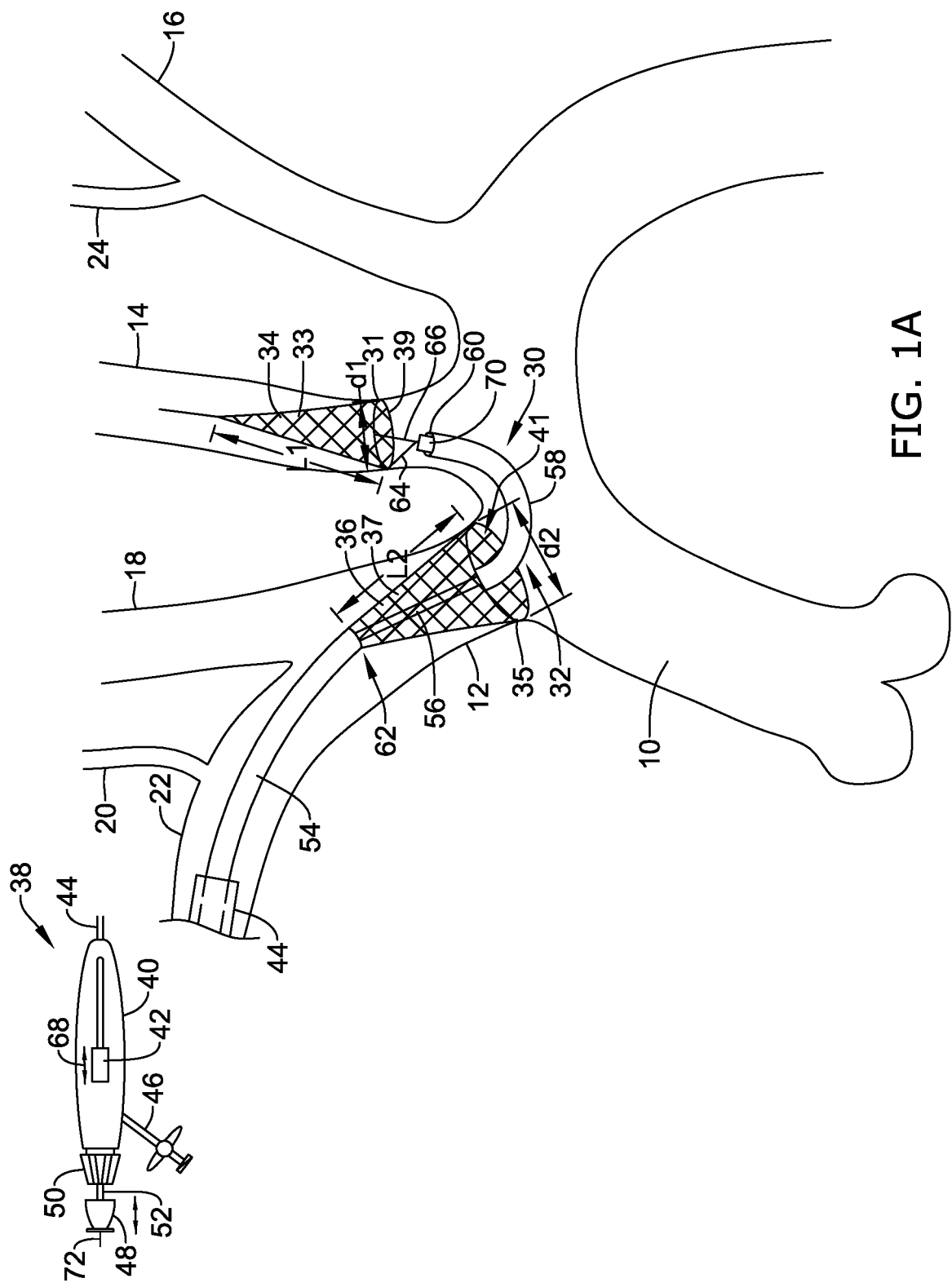
FIGS. 1A and 1B illustrate a first embodiment for deploying three filters to protect the cerebral vascular architecture.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The currently marketed Sentinel system made by Claret Medical and embodiments of which are described in U.S. Pat. No. 9,492,264 mentioned above has two filters, a first which protects the right brachiocephalic artery, from which the right vertebral and right common carotid arteries typically originate, and a second filter in the left common carotid artery. In a typical patient, the left vertebral artery which provides approximately seven percent of the perfusion to the brain is left unprotected.

One disclosed solution to protecting the left vertebral is the use of a second device intended to be placed in the left arm, e.g. through the left radial artery, with a filter placed in the left subclavian from which the left vertebral typically originates. Embodiments of such a solution can be found in U.S. Pat. No. 9,566,144, the entirety of which is hereby incorporated by reference herein.

The present application discloses several multi-vessel embodiments which may include compound systems of filters and/or deflectors that can provide full cerebral protection.

The disclosure generally relates to devices and methods for filtering fluids and/or deflecting debris contained within fluids, including body fluids such as blood. A filtering or deflecting device can be positioned in an artery before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc.) to inhibit or prevent embolic material such as debris, emboli, thrombi, etc. resulting from entering the cerebral vasculature.

The devices may be used to trap and/or deflect particles in other blood vessels within a subject, and they can also be used outside of the vasculature. The devices described herein are generally adapted to be delivered percutaneously to a target location within a subject, but can be delivered in any suitable way and need not be limited to minimally-invasive procedures.

FIG. 1A is a schematic view of an aortic arch 10 including a first protection device 30. The aortic arch 10 is upstream of the left and right coronary arteries (not explicitly shown). The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to, and may be directly accessed from (termed right radial access), the right arm. The left subclavian artery 16 branches to the left vertebral artery 24, usually in the shoulder area. The left subclavian artery 16 supplies blood to, and may be directly accessed from (termed left radial axis), the left arm. Four of the arteries illustrated in FIG. 1A supply blood to the cerebral vasculature: (1) the left carotid artery 14 (about 40% of cerebral blood supply); (2) the right carotid artery 18 (about 40% of cerebral blood supply); (3) the right vertebral artery 20 (about 10% of cerebral blood supply); and (4) the left vertebral artery 24 (about 10% of cerebral blood supply).

It may be desirable to filter blood flow to all four arteries 14, 18, 20, 24 supplying blood to the brain and/or deflect particulates from entering the arteries 14, 18, 20, 24 supplying the brain. It may also be desirable to limit the number of incision sites or cuts required to deploy the system(s). FIG. 1A illustrates a first step in deploying a multi-filter system using a right radial access incision.

The first protection device 30 may include a distal end region 32 and a proximal end region 38. The proximal end region 38 may be configured to be held and manipulated by a user such as a surgeon. The distal end region 32 may be configured to be positioned at a target location such as, but not limited to, the innominate artery 12 and/or the left common carotid artery 14. When the distal end region 32 is so deployed, blood is filtered prior to entering the left common carotid artery 14, the right common carotid artery 18, and the right vertebral artery 20.

The proximal end region 38 may include a handle 40, a control 42 such as a slider, an outer sheath 44, a port 46, an inner member translation control 48 such as a knob, and hemostasis valve control 50 such as a knob. In some embodiments, the handle 40 may include fewer or more control elements than those illustrated in FIG. 1A. The proximal end region may also include an inner member 52 radially inward of the outer sheath 44. While not explicitly shown, the proximal end region 38 may also include a filter wire 66 radially inward of the outer sheath 44 (and sometimes radially outward of the inner member 52). Some illustrative filter wires are described in commonly assigned U.S. Pat. No. 9,566,144, the entirety of which is hereby incorporated by reference.

The slider 42 can be used to translate the outer sheath 44 and/or a filter assembly 36 (e.g., coupled to a proximal shaft 54). For example, the slider 42 may proximally retract the outer sheath 44, the slider 42 may distally advance the filter assembly 36 out of the outer sheath 44, or the slider 42 may proximally retract the outer sheath 44 and distally advance the proximal filter assembly 36 (e.g., simultaneously or serially), which can allow the proximal filter assembly 36 to radially expand. The slider 42 may also be configured to have an opposite translation effect, which can allow the filter assembly 36 to be radially collapsed (e.g., due to compression by the outer sheath 44) as the filter assembly 36 is drawn into the outer sheath 44. Other deployment systems are also possible, for example comprising gears or other features such as helical tracks (e.g., configured to compensate for any differential lengthening due to foreshortening of the filter assembly 36, configured to convert rotational motion into longitudinal motion), a mechanical element, a pneumatic element, a hydraulic element, etc. for opening and/or closing the filter assembly 36. While not explicitly shown, the handle 40 may include a similar mechanism for manipulating the distal filter assembly 34 via the filter wire 66, the inner member 52 and/or the guiding member 60.

The port 46 is in fluid communication with the inner member 52 (e.g., via a Y-shaped connector in the handle 40). The port 46 can be used to flush the device (e.g., with saline) before, during, and/or after use, for example to remove air. The port 46 can additionally, or alternatively, be used to monitor blood pressure at the target location, for example by connecting an arterial pressure monitoring device in fluid communication with a lumen of the outer sheath 44. The port 46 can be also or alternatively be used to inject contrast agent, dye, thrombolytic agents such as tissue plasminogen activator (t-PA), etc. The slider 42 may be independent of the inner member 52 such that the inner member 52 is longitudinally movable independent of the proximal filter assembly 36 and the outer sheath 44 (and/or the distal filter assembly 34, the filter wire 66, inner member 52, or the guiding member 60). The inner member translation control 48 can be used to longitudinally translate the inner member 52, for example before, after, and/or during deployment of the filter assembly 36. The inner member translation control 48 may comprise a slider in the handle 40 (e.g., separate from the slider 42).

The rotatable hemostasis valve control 50 can be used to reduce or minimize fluid loss through the protection device 30 during use. For example, a proximal portion and/or intermediate region of the protection device may be positioned in the right subclavian artery 22 and the direction of blood flow with respect to the device 30 will be distal to proximal, so blood may be otherwise inclined to follow the pressure drop out of the device 30. The hemostasis valve control 50 is illustrated as being rotatable, but other arrangements are also possible (e.g., longitudinally displaceable). The hemostasis valve control 50 may be configured to fix relative positions of the outer sheath 44 and the filter assembly 36, for example as described with respect to the hemostasis valve in U.S. Pat. No. 8,876,796. The hemostasis valve 50 may comprise, for example, an elastomeric seal and HV nut.

The distal end region 32 may include a first or distal filter assembly 34 configured to be deployed within the left common carotid artery 14 and a second or proximal filter assembly 36 configured to deployed within the innominate artery 12. The distal end region 32 may further include a proximal (or outer) sheath 44, a proximal shaft 54 coupled to an expandable proximal filter assembly 36, a distal shaft 56 coupled to a distal articulatable sheath 58, a distal filter assembly 34, and guiding member 60.

The proximal shaft 54 is co-axial with proximal sheath 44, and a proximal region 62 of proximal filter assembly 36 is secured to proximal shaft 54. In its collapsed configuration (not explicitly shown), the proximal filter assembly 36 may be disposed within proximal sheath 44 and is disposed distally relative to proximal shaft 54. The proximal sheath 44 may be axially (e.g., distally and proximally) movable relative to proximal shaft 54 and the proximal filter assembly 36. The system 30 may also include a distal sheath 58 secured to a distal region of the distal shaft 56. The distal shaft 56 may be co-axial with the proximal shaft 54 and the proximal sheath 44. The distal sheath 58 and distal shaft 56 may be secured to one another and axially movable relative to the proximal sheath 44, the proximal shaft 54, and the proximal filter assembly 36. The system 30 may also include a distal filter assembly 34 carried by the guiding member 60. While not explicitly shown, the distal filter assembly 34 may be maintained in a collapsed configuration within the distal sheath 58. The guiding member 60 may be coaxial with distal sheath 58 and distal shaft 56 as well as proximal sheath 44 and proximal shaft 54. The guiding member 60 may be axially movable relative to distal sheath 58 and distal shaft 56 as well as proximal sheath 44 and proximal shaft 54. The proximal sheath 44, the distal sheath 58, and the guiding member 60 may each be adapted to be independently moved axially relative to one other. That is, the proximal sheath 44, the distal sheath 58, and the guiding member 60 are adapted for independent axial translation relative to each of the other two components. It is contemplated that the handle 40 may include control elements (such as, but not limited to, slides, switches, buttons, dials, etc.) configured to individually actuate the proximal sheath 44, the distal sheath 58, and the guiding member 60.

The proximal filter assembly 36 may include a support element or frame 35 and a filter element 37. Similarly, the distal filter assembly 34 includes support element 31 and a filter element 33. The frames 31, 35 may generally provide expansion support to the filter elements 33, 37 in the expanded state. In the expanded state, the filter elements 33, 37 are configured to filter fluid (e.g., blood) flowing through the filter elements 33, 37 and to inhibit or prevent particles (e.g., embolic material) from flowing through the filter elements 33, 37 by capturing the particles in the filter elements 33, 37. The frames 31, 35 are configured to engage or appose the inner walls of a lumen (e.g., blood vessel) in which the filter assembly 34, 36 is expanded. The frames 31, 35 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The frames 31, 35 may comprise a wire (e.g., having a round (e.g., circular, elliptical) or polygonal (e.g., square, rectangular) cross-section). For example, in some embodiments, the frames 31, 35 comprises a straight piece of nitinol wire shape set into a circular or oblong hoop or hoop with one or two straight legs running longitudinally along or at an angle to a longitudinal axis of the filter assembly 34, 36. At least one of the straight legs may be coupled to a filter wire 66 or a strut 64, as shown with respect to the distal filter assembly 34. The straight legs may be on a long side of the filter assembly 34, 36 and/or on a short side of the filter assembly 34, 36. The frames 31, 35 may form a shape of an opening 39, 41 of the filter assembly 34, 36. The opening 39, 41 may be circular, elliptical, or any shape that can appropriately appose sidewalls of a vessel such as the left subclavian artery or the left vertebral artery. The filter assembly 34, 36 may have a generally proximally-facing opening 39, 41. In other embodiments, the opening 39, 41 may be distally facing. The orientation of the opening 39, 41 may vary depending on where the access incision is located. For example, as shown in FIG. 1A, the proximal filter assembly 36 has a generally distally-facing opening 41, and the distal filter assembly 34 has a generally proximally-facing opening 39 relative to the device 30. The filter assemblies 34, 36 can be thought of as facing opposite directions.

The frames 31, 35 may include a radiopaque marker such as a small coil wrapped around or coupled to the hoop to aid in visualization under fluoroscopy. In some embodiments, the frame may comprise a shape other than a hoop, for example, a spiral. In some embodiments, the filter assembly 34, 36 may not include or be substantially free of a frame.

In some embodiments, the frames 31, 35 and the filter elements 33, 37 form an oblique truncated cone having a non-uniform or unequal length around and along the length of the filter assembly 34, 36. In such a configuration, along the lines of a windsock, the filter assembly 34, 36 has a larger opening 39, 41 (upstream) diameter and a reduced ending (downstream) diameter.

The filter elements 33, 37 may include pores configured to allow blood to flow through the filter elements 33, 37, but that are small enough to inhibit prevent particles such as embolic material from passing through the filter elements 33, 37. The filter elements 33, 37 may comprise a filter membrane such as a polymer (e.g., polyurethane, polytetrafluoroethylene (PTFE)) film mounted to the frame 31, 35. The filter element may have a thickness between about 0.0001 inches and about 0.03 inches (e.g., no more than about 0.0001 inches, about 0.001 inches, about 0.005 inches, about 0.01 inches, about 0.015 inches, about 0.02 inches, about 0.025 inches, about 0.03 inches, ranges between such values, etc.).

The film may comprise a plurality of pores or holes or apertures extending through the film. The film may be formed by weaving or braiding filaments or membranes and the pores may be spaces between the filaments or membranes. The filaments or membranes may comprise the same material or may include other materials (e.g., polymers, non-polymer materials such as metal, alloys such as nitinol, stainless steel, etc.). The pores of the filter elements 33, 37 are configured to allow fluid (e.g., blood) to pass through the filter elements 33, 37 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration verses fluid volume. The pores may be laser drilled into or through the filter elements 33, 37, although other methods are also possible (e.g., piercing with microneedles, loose braiding or weaving). The pores may have a lateral dimension (e.g., diameter) between about 10 micron (μm) and about 1 mm (e.g., no more than about 10 μm, about 50 μm, about 100 μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured.

The material of the filter elements 33, 37 may comprise a smooth and/or textured surface that is folded or contracted into the delivery state by tension or compression into a lumen. A reinforcement fabric may be added to or embedded in the filter elements 33, 37 to accommodate stresses placed on the filter elements 33, 37 during compression. A reinforcement fabric may reduce the stretching that may occur during deployment and/or retraction of the filter assembly 34, 36. The embedded fabric may promote a folding of the filter to facilitate capture of embolic debris and enable recapture of an elastomeric membrane. The reinforcement material could comprise, for example, a polymer and/or metal weave to add localized strength. The reinforcement material could be imbedded into the filter elements 33, 37 to reduce thickness. For example, imbedded reinforcement material could comprise a polyester weave mounted to a portion of the filter elements 33, 37 near the longitudinal elements of the frames 31, 35 where tensile forces act upon the frames 31, 35 and filter elements 33, 37 during deployment and retraction of the filter assembly 34, 36 from the outer sheath 44 and/or the distal sheath 58.

In some cases, the filter assembly 34, 36 may include a self-expanding filter assembly (e.g., comprising a superelastic material with stress-induced martensite due to confinement in the outer sheath 44 and/or the distal sheath 58). The filter assembly 34, 36 may comprise a shape-memory material configured to self-expand upon a temperature change (e.g., heating to body temperature). The filter assembly 34, 36 may comprise a shape-memory or superelastic frame (e.g., comprising a distal end hoop comprising nitinol) and a microporous material (e.g., comprising a polymer including laser-drilled holes) coupled to the frame, for example similar to the filter assemblies described in U.S. Pat. No. 8,876,796.

The filter assembly 34, 36 may be coupled (e.g., crimped, welded, soldered, etc.) to a distal end of a deployment wire or filter wire 66 via a strut or wire 64, although this is not required. When both or all of the filter wire 66 and the strut 64 are provided, the filter wire 66 and the strut 64 may be coupled within the guiding member 60 proximal to the filter assembly 34 using a crimp mechanism. In other embodiments, the filter wire 66 and the strut 64 may be a single unitary structure. The filter wire 66 and/or strut 64 can comprise a rectangular ribbon, a round (e.g., circular, elliptical) filament, a portion of a hypotube, a braided structure (e.g., as described herein), combinations thereof, and the like. The filter wire 66 can be coupled to the handle 40 and/or a slider to provide differential longitudinal movement versus the outer sheath 44, as shown by the arrows 68, which can sheathe and unsheathe the distal filter assembly 34 from the distal sheath 58. Similarly, the proximal filter assembly 36 may be unsheathe through actuation of a mechanism on the handle 40 or through movement of the handle 40 itself.

The filter assembly 34, 36 in an expanded, unconstrained state has a maximum diameter or effective diameter (e.g., if the mouth is in the shape of an ellipse) d1, d2. The diameter d1, d2 can be between about 1 mm and about 15 mm (e.g., at least about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, ranges between such values, etc.). In some embodiments, the diameter d1, d2 is between about 7 mm and about 12 mm (e.g., about 7 mm, about 8 mm, about 9 mm, about 10 mm, about 11 mm, about 12 mm, ranges between such values, etc.). In some embodiments, the diameter d is between about 2 mm and about 4.5 mm (e.g., about 2 mm, about 2.5 mm, about 3 mm, about 3.5 mm, about 4 mm, about 4.5 mm, ranges between such values, etc.). Other diameters d1, d2 or other types of lateral dimensions are also possible. Different diameters d1, d2 can allow treatment of a selection of subjects having different vessel sizes.

The filter assembly 34, 36 has a maximum length L1, L2. The length L1, L2 can be between about 7 mm and about 50 mm (e.g., at least about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 30 mm, about 35 mm, about 40 mm, about 45 mm, about 50 mm, ranges between such values, etc.). Other lengths L1, L2 are also possible, for example based on the diameter or effective diameter d1, d2. For example, the length L1, L2 of the filter assembly 34, 36 may increase as the diameter d1, d2 increases, and the length L1, L2 of the filter assembly 34, 36 may decrease as the diameter d1, d2 decreases. A distance from an apex of the mouth of the filter assembly 34, 36 to an elbow in the frame may be about 35 mm. Different lengths L1, L2 can allow treatment of a selection of subjects having different vessel sizes.

Figure 1B:
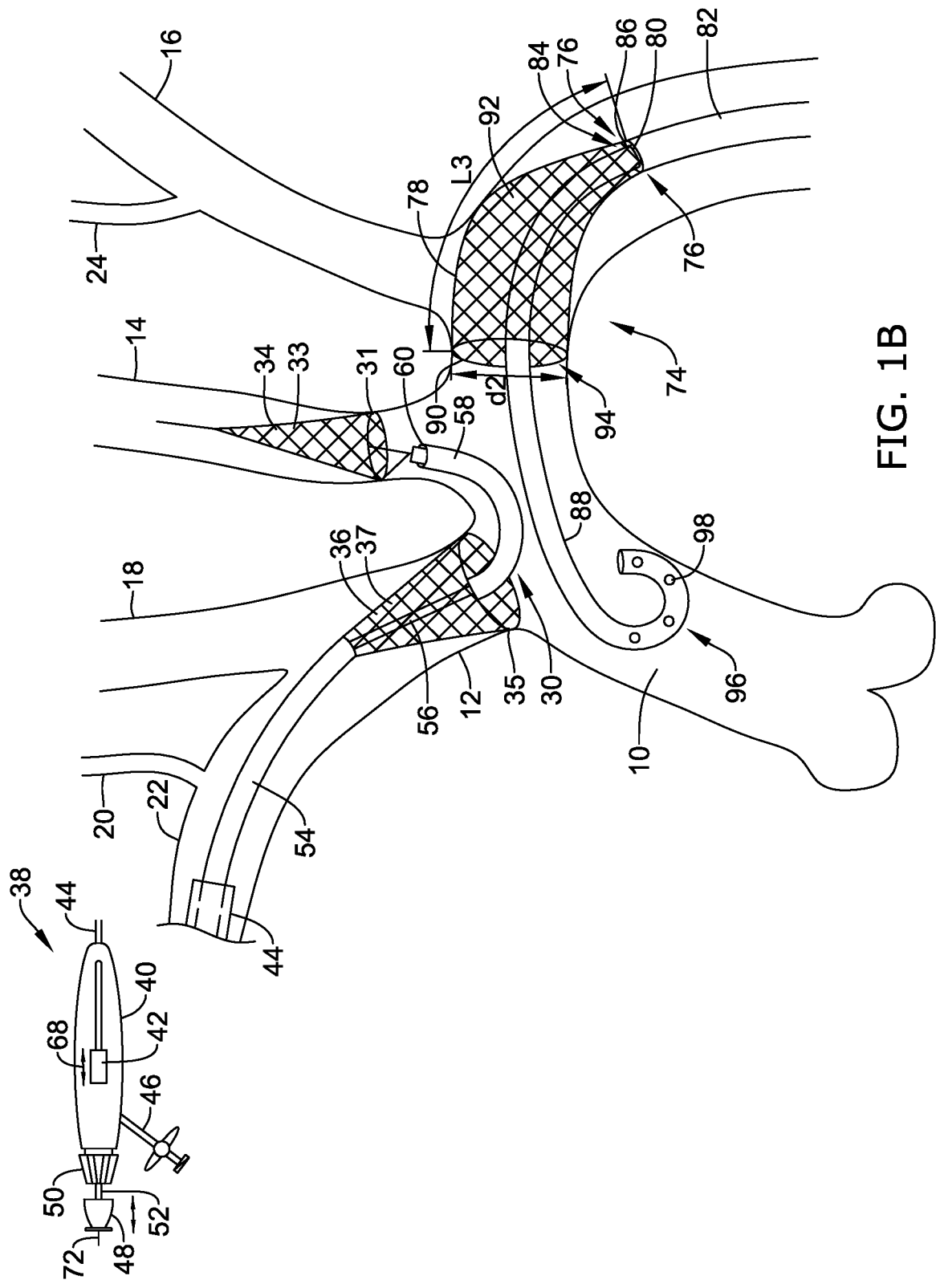

As described in more detail below, the distal sheath 58 may be adapted to be steered, or bent, relative to the proximal sheath 44 and the proximal filter assembly 36. As the distal sheath 58 is steered, the relative directions in which the openings face will be adjusted. Regardless of the degree to which the distal sheath 58 is steered, the filter assemblies 34, 36 are still considered to having openings facing opposite directions. For example, the distal sheath 58 could be steered to have an approximately 180 degree bend, in which case the filter assemblies 34, 36 would have openings 39, 41 facing in substantially the same direction, as shown in FIG. 1B. The directions of the filter openings 41, 39 are therefore described if the system were to assume a substantially straightened configuration (not explicitly shown). The proximal filter element 37 may taper down in the proximal direction from support element 35, while the distal filter element 33 may taper down in the distal direction from support element 31. A fluid, such as blood, flows through the opening and passes through the pores in the filter elements 33, 37, while the filter elements 33, 37 are adapted to trap foreign particles therein and prevent their passage to a location downstream of the filter assemblies.

The filter assemblies 34, 36 may be secured to separate system components. For example, the proximal filter assembly 36 is secured to the proximal shaft 54, while the distal filter assembly 34 is secured to guiding member 60. In FIG.

1A, the filters assemblies, 36 are secured to independently actuatable components. This may allow the filters assemblies, 36 to be independently positioned and controlled. Additionally, the filter assembles 34, 36 may be collapsed within two different tubular members in their collapsed configurations. For example, the proximal filter assembly 36 is collapsed within proximal sheath 44, while the distal filter assembly 34 is collapsed within distal sheath 58. In the system's delivery configuration, the filter assemblies 34, 36 are axially-spaced from one another. For example, in FIG. 1A, the distal filter assembly 34 is distally-spaced relative to proximal filter assembly 36. However, in an alternative embodiment, the filter assemblies 34, 36 may be positioned such that a first filter is located within a second filter.

In some embodiments, the distal sheath 58 and the proximal sheath 44 have substantially the same outer diameter. When the filter assemblies 34, 36 are collapsed within the respective sheaths 58, 44, the sheath portion of the system 30 therefore has a substantially constant outer diameter, which can ease the delivery of the system 30 through the patient's body and increase the safety of the delivery. The distal and proximal sheaths 58, 44 may have substantially the same outer diameter, both of which have larger outer diameters than the proximal shaft 54. The proximal shaft 54 may have a larger outer diameter than the distal shaft 56, wherein the distal shaft 56 is disposed within the proximal shaft 54. The guiding member 60 may have a smaller diameter than the distal shaft 56. In some embodiments, the proximal and distal sheaths 44, 58 have an outer diameter between 3 French (F) and 14 F. In certain embodiments, the outer diameter is between 4 F and 8 F. In still other embodiments, the outer diameter is between 4 F and 6 F. In some embodiments, the sheaths 44, 58 have different outer diameters. For example, the proximal sheath 44 can have a size of 6 F, while the distal sheath 58 has a size of 5 F. In an alternate embodiment the proximal sheath 44 is 5 F and the distal sheath 58 is 4 F. These are just examples and are not intended to limit the sheaths 44, 58 to a particular size. A distal sheath 58 with a smaller outer diameter than the proximal sheath 44 reduces the delivery profile of the system 30 and can ease delivery.

In some methods of use, the filter system 30 is advanced into the subject through an incision made in the subject's right radial artery, or alternatively the right brachial artery. In a variety of medical procedures, a medical instrument is advanced through a subject's femoral artery, which is larger than the right radial artery. A delivery catheter used in femoral artery access procedures has a larger outer diameter than would be allowed in a filter system advanced through a radial artery. Additionally, in some uses the filter system is advanced from the right radial artery into the aorta via the brachiocephalic trunk. The radial artery has the smallest diameter of the vessels through which the system is advanced. The radial artery therefore limits the size of the system that can be advanced into the subject when the radial artery is the access point. The outer diameters of the systems described herein, when advanced into the subject via a radial artery, are therefore smaller than the outer diameters of the guiding catheters (or sheaths) typically used when access is gained via a femoral artery. In some embodiments, the system 30 may be advanced over a guidewire 72, although this is not required.

The system 30 may be delivered to the left carotid artery 14 and the innominate artery 12 in a delivery configuration. The system's delivery configuration generally refers to the configuration where both filter assemblies 34, 36 are in collapsed configurations within the system (e.g., within the distal and proximal sheaths 58, 44). The distal articulating sheath 58 may be independently movable with 3 degrees of freedom relative to the proximal sheath 44 and proximal filter assembly 36. In some embodiments, the proximal sheath 44 and the distal sheath 58 may be releasably coupled together. For example, the proximal sheath 44 can be coupled to the distal sheath 58 using an interference fit, a friction fit, a spline fitting, end to end butt fit or any other type of suitable coupling between the two sheaths 44, 58. When coupled together, the components move as a unit. For example, the proximal sheath 44, the proximal shaft 54, the proximal filter assembly 36, the distal shaft 56, and the distal filter assembly 34 will rotate and translate axially (in the proximal or distal direction) as a unit. When the proximal sheath 44 is retracted to allow the proximal filter assembly 36 to expand, the distal sheath 58 can be independently rotated, steered, or translated axially (either in the proximal direction or distal direction). The distal sheath 58 therefore has 3 independent degrees of freedom: axial translation, rotation, and steering. The adaptation to have 3 independent degrees of freedom is advantageous when positioning the distal sheath 58 in a target location, details of which are described below.

The system 30 is advanced into the subject's right radial artery through an incision in the right arm, or alternately through the right brachial artery. The system is advanced through the right subclavian artery 22 and into the brachiocephalic or innominate artery 12, and a portion of the system is positioned within the aortic arch 10. The proximal sheath 44 is retracted proximally to allow proximal filter support element 35 to expand to an expanded configuration against the wall of the innominate artery 12, as is shown in FIG. 1A. The proximal filter element 37 is secured either directly or indirectly to support element 35 and is therefore reconfigured to the configuration shown in FIG. 1A. The position of distal sheath 58 can be substantially maintained while proximal sheath 44 is retracted proximally. Once expanded, the proximal filter assembly 36 filters blood traveling through the innominate artery 12, and therefore filters blood traveling into the right common carotid artery 18 and the right vertebral artery 20. The expanded proximal filter assembly 36 is therefore in position to prevent foreign particles from traveling into the right common carotid artery 18 and the right vertebral artery 20 and into the cerebral vasculature.

The distal sheath 58 is then steered, or bent, and the distal end 70 of the distal sheath 58 is advanced into the left common carotid artery 14. The guiding member 60 is thereafter advanced distally relative to distal sheath 58, allowing the distal support element 31 to expand from a collapsed configuration to a deployed configuration against the wall of the left common carotid artery 14, as shown in FIG. 1A. The distal filter element 33 is also reconfigured into the configuration shown in FIG. 1A. Once expanded, the distal filter assembly 34 filters blood traveling through the left common carotid artery 14. In some embodiments, the distal filter assembly 34 may be deployed prior to the deployment of the proximal filter assembly 36. The distal filter assembly 34 is therefore in position to trap foreign particles and prevent them from traveling into the cerebral vasculature.

After the first filter system 30 has been positioned (or substantially simultaneously therewith or prior to implantation of the first system 30), a second protection device or filter system 74 may be deployed, as shown in FIG. 1B. In some embodiments, the second filter system 74 may be positioned within the aortic arch 10, although this is not required.

The protection device, or filter system, 74 comprises a proximal portion (not explicitly shown) and a distal portion 76 including a filter assembly 78. The proximal portion may be coupled to a handle (not explicitly shown) configured to remain outside the body. In some cases, the handle of the second protection device 74 may be similar in form and function to the handle 40 described herein. The proximal portion is configured to be held and manipulated by a user such as a surgeon. The distal portion 76 is configured to be positioned at a target location, such as, but not limited to, the aortic arch 10. When the distal portion 76 is configured to be positioned within the aortic arch 10, the location may be upstream of the left subclavian artery 16 such that the blood is filtered prior to entering the left subclavian artery 16 and thus prior to entering the left vertebral artery 24.

The distal portion 76 may include outer sheath 82 and an inner tubular member 80 coupled to the filter assembly 78. The inner tubular member 80 may define a lumen 84 extending from a proximal end (not explicitly shown) to the distal end 86 thereof. The lumen 84 may be configured to receive other medical devices, including, but not limited to an angiography or pigtail catheter 88, a procedural catheter (such as, but not limited to a TAVR or TAVI procedural catheter or device), etc. The pigtail catheter 88 may be radially inward of the inner tubular member 80 and the inner tubular member 80 may be radially inward of the outer sheath 82. The filter assembly 78 may be radially between the outer sheath 82 and the pigtail catheter 88 (e.g., radially inward of the outer sheath 82 and the pigtail catheter 88 radially inward of the filter assembly 78) in a delivery state or shape or position. While not explicitly shown, the second protection device 74 may include a filter wire (not explicitly shown) or a guidewire radially inward of the inner tubular member 80 and/or the pigtail catheter 88. The outer sheath 82 and/or the inner tubular member 80 may have a diameter large enough for a procedural catheter to pass therethrough. The outer sheath 82 may comprise an atraumatic distal tip. The protection device 74 and other protection devices described herein may be flexible and/or atraumatic. The outer sheath 82 may comprise a curvature, for example based on an intended placement location (e.g., the aortic arch).

The handle (not explicitly shown) can be used to translate the outer sheath 82 and/or a filter assembly 78 (e.g., coupled to the inner tubular member 80). For example, the handle may include a mechanism to proximally retract the outer sheath 82, distally advance the filter assembly 78 out of the outer sheath 82, or both proximally retract the outer sheath 82 and distally advance the filter assembly 78 (e.g., simultaneously or serially), which can allow the filter assembly 78 to radially expand. The handle may also be configured to have an opposite translation effect, which can allow the filter assembly 78 to be radially collapsed (e.g., due to compression by the outer sheath 82) as the filter assembly 78 is drawn into the outer sheath 82. Other deployment systems are also possible, for example comprising gears or other features such as helical tracks (e.g., configured to compensate for any differential lengthening due to foreshortening of the filter assembly 78, configured to convert rotational motion into longitudinal motion), a mechanical element, a pneumatic element, a hydraulic element, etc. for opening and/or closing the filter assembly 78.

The filter assembly 78 may include a support element or frame 90 and a filter element 92. In some embodiments, the filter assembly 78 may be a stent supported filter. The frame 90 may generally provide expansion support to the filter element 92 in the expanded state. The frame 90 may be similar in form and function to the frames 31, 35 described herein. Similarly, the filter element 92 may be similar in form and function to the filter element 33 described herein. The support element 90 generally provides expansion support to the filter element 92 in its expanded configurations, while the filter element 92 is adapted to filter fluid, such as blood, and trap particles flowing therethrough. The expansion support 90 is adapted to engage the wall of the lumen in which it is expanded. In some embodiments, the filter assembly 78 may be self-expanding. The filter element 92 has pores therein that are sized to allow the blood to flow therethrough, but are small enough to prevent unwanted foreign particles from passing therethrough. The foreign particles are therefore trapped by and within the filter element 92. It is contemplated that the filter assembly 78 may have one or more openings configured to allow another device (such as the pigtail catheter 88 or a procedural catheter) to pass therethrough.

As shown in FIG. 1B, the filter assembly 78 has a generally distally-facing opening 94. In other embodiments, the opening 94 may be proximally facing. The orientation of the opening 94 may vary depending on where the access incision is located and/or the vessel in which it is deployed.

The filter assembly 78 in an expanded, unconstrained state has a maximum diameter or effective diameter (e.g., if the mouth is in the shape of an ellipse) d3. The diameter d3 can be between about 1 mm and about 40 mm. In some embodiments (e.g., when the filter assembly is configured to be positioned in the aortic arch), the diameter d3 is between about 20 mm and about 35 mm. In other embodiments (e.g., when the filter assembly is configured to be positioned in the left subclavian artery), the diameter d3 is between about 7 mm and about 12 mm. In yet other embodiments (e.g., when the filter assembly is configured to be positioned in the left vertebral artery), the diameter d3 is between about 2 mm and about 4.5 mm. Other diameters d3 or other types of lateral dimensions are also possible. Different diameters d3 can allow treatment of a selection of subjects having different vessel sizes.

The filter assembly 78 has a maximum length L3. The length L3 can be between about 7 mm and about 50 mm. Other lengths L3 are also possible, for example based on the diameter or effective diameter D3. For example, the length L3 of the filter assembly 78 may increase as the diameter D3 increases, and the length L3 of the filter assembly 78 may decrease as the diameter D3 decreases. A distance from an apex of the mouth of the filter assembly 78 to an elbow in the frame may be about 35 mm. Different lengths L can allow treatment of a selection of subjects having different vessel sizes.

The distal portion 76 may include fluoroscopic markers to aid a user in positioning the device 74, deploying the filter assembly 78, utilizing the pigtail catheter 88, etc. A fluoroscopic marker (not explicitly shown) may be positioned proximate to a distal end of the outer sheath 82. Another fluoroscopic marker (not explicitly shown) may be positioned proximate to a proximal end of the filter assembly 78. In some cases, another fluoroscopic marker (not explicitly shown) may be proximate to a distal end of the filter assembly 78. Another fluoroscopic marker (not explicitly shown) may be proximate to a distal end of the inner member 80. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some embodiments, the protection device 74 may include a guidewire (not explicitly shown) extending therethrough, although the guidewire may be characterized as being separate from the protection device 74, for example independently sold, packaged, and/or directed. The guidewire may extend through a lumen of the outer sheath 82, the inner tubular member 80 and/or the pigtail catheter 88. The lumen of the outer sheath 82, the inner tubular member 80, and/or the pigtail catheter 88 may be configured to receive a guidewire having a diameter between about 0.014 inches (0.356 mm) and about 0.025 inches (0.635 mm). If so provided, the guidewire may extend through a lumen of the filter assembly 78. For example, any portion of the protection device 74 may be tracked over the guidewire to position the protection device 74 at a desired location.

The filter assembly 78 may be positioned, for example, in the aortic arch 10, to protect the cerebral vasculature (e.g., the left vertebral artery 24) from embolic debris during an endovascular procedure such as TAVI. While the procedure is described as positioning the second filter assembly 78 in the aortic arch, the method is not limited to positioning the second filter assembly 78 within the aortic arch 10. The second filter assembly 78 may be positioned within other arteries (or other lumens), as desired, such as, but not limited to the left subclavian artery 16 or the left vertebral artery 24. The filter assembly 78 may be positioned in the aortic arch 10 upstream of the left subclavian artery 16. The user may choose a protection device 74 comprising a distal-facing filter assembly 78 having a diameter appropriate for the artery (or another lumen) in which it is to be deployed. The protection device 74 may be packaged in a sterile coiled packaging. The outer sheath 82 may include a curvature, for example complementing the size and orientation of the filter assembly 78. The outer sheath 82 and/or the inner tubular member 80 may be steerable (e.g., a pull wire-controlled sheath).

Lumens of the protection device 74, for example a lumen of the outer sheath 82, a lumen of the inner member 80, and/or a lumen of the pigtail catheter 88, may be flushed (e.g., using saline) once or several times before, during, and/or after the procedure. The filter assembly 78 of the protection device 74 may be flushed and/or submerged (e.g., in a bowl of saline). Flushing and/or submerging of the filter assembly 78 may be with the filter assembly 78 in the outer sheath 82 (e.g., in the compressed state) and/or with the filter assembly 78 out of the outer sheath 82 (e.g., in the deployed state). If the filter assembly 78 is flushed and/or submerged in the deployed state, the filter assembly 78 may be compressed into the outer sheath 82 before use.

The right femoral artery may be accessed using an introducer. The outer sheath 82 is steered, into or towards the aortic arch 10. In some cases, the outer sheath 82 may be advanced over a guidewire, although this is not required. In some implementations, the guidewire and the outer sheath 82 and/or inner member 80 (and the filter assembly 78 coupled thereto) may be tracked together, with the guidewire leading the outer sheath 82 and/or inner member 80 (e.g., advance the guidewire a distance, then advance the outer sheath 82 and/or the inner member 80 over the guidewire approximately the same distance). In some cases, where the guidewire is floppy or lacks rigidity, it may be introduced inside the outer sheath 82 and then advanced ahead of the inner member 80 in the vasculature. The guidewire may be advanced at least about 6 centimeters (cm) distal to the distal end of the outer sheath 82 and/or inner member 80, although this is not required.

The outer sheath 82 may be curved and/or steerable to facilitate navigation from the femoral artery to the aortic arch 10. The inner tubular member 80 may be advanced simultaneously with or serially to the outer sheath 82. Additionally, the pigtail catheter 88 may be advanced simultaneously with or serially to the inner tubular member 80 and/or the outer sheath 82. Once the outer sheath 82 is positioned in or adjacent to the aortic arch 10, the pigtail catheter 88 may be advanced distally from the outer sheath 80. A distal end region 96 of pigtail catheter 88 may have a generally arcuate shape (although this is not required) and may include one or more apertures 98 therein. The one or more apertures 98 may be in fluid communication with a lumen and may be configured to deliver a radiopaque fluid or contrast fluid.

Tracking of the protection device 74 may be performed under fluoroscopy, for example using radiopaque markers (e.g., at a distal end of the outer sheath 82 and/or the inner tubular member 80) and/or radiopaque fluid or contrast media. Radiopaque fluid may be provided through the inner tubular member 80, the pigtail catheter 88, and/or the outer sheath 82. The protection device 74 may be positioned so that the filter assembly 78 is upstream of the left vertebral artery 24 or proximate to the ostium of the left subclavian artery 16 so that the filter assembly 78 can inhibit or prevent embolic material from entering the cerebral vasculature through the left vertebral artery 24. However, it is contemplated that positioning may be based on available anatomy.

During navigation through the vasculature, the filter assembly 78 may be disposed within a lumen of the outer sheath 82 and held in a collapsed position therein until the filter assembly 78 is advanced distally from the outer sheath 82 and/or the outer sheath 82 is proximally retracted relative to the filter assembly 78. After the pigtail catheter 88 has been deployed, the outer sheath 82 may then be proximally retracted (and/or the inner tubular member 80 distally advanced) to deploy the filter assembly 78. In some cases, the filter assembly 78 may be deployed before advancing the pigtail catheter 88, or substantially simultaneously therewith. The filter assembly 78 may be positioned to direct any dislodged debris downstream away from the left subclavian artery 16 and the left vertebral artery 24.

Once the protection device 74 is in position, the filter assembly 78 may be deployed from the outer sheath 82. For example, the outer sheath 82 may be proximally retracted and/or the filter assembly 78 may be distally advanced. Radiopaque markers, for example on the filter assembly 78 can help determine when the filter assembly 78 achieves a deployed state. Differential longitudinal movement of the filter assembly 78 and the outer sheath 82 can cease upon full or appropriate deployment of the filter assembly 78. Apposition of the filter assembly 78 with sidewalls of the aortic arch 10 can be verified, for example using radiopaque fluid or contrast media. Radiopaque fluid may be provided through the pigtail catheter 88, the inner tubular member 80, and/or the outer sheath 82. If the radiopaque fluid is able to flow between the frame of the filter assembly 78 and the sidewalls of the aortic arch, then the filter assembly 78 may be improperly positioned (e.g., indicative of inadequate deployment, inadequate sizing, calcium, etc.). The filter assembly 78 may be retracted back into the outer sheath 82 and redeployed, or a different protection device may be used. After positioning of the protection device 74, the pigtail catheter 88 may be withdrawn and the procedural catheter advanced through the lumen of the inner tubular member 80 and the filter assembly 78. Together, the first protection device 30 and the second protection device 74 may protect all four cerebral arteries 14, 18, 20, 24 during a procedure.

The protection device(s) 30, 74 can thereafter be removed from the subject (or at any point in the procedure). In an exemplary embodiment, the distal filter assembly 34 is first retrieved back within distal sheath 58 to the collapsed configuration. To do this, the guiding member 60 is retracted proximally relative to the distal sheath 58. This relative axial movement causes the distal sheath 58 to engage a strut or wire 64 and begin to move strut 64 towards guiding member 60. The support element 31, which is coupled to the strut 64, begins to collapse upon the collapse of the strut 64. The filter element 33 therefore begins to collapse as well. Continued relative axial movement between the guiding member 60 and the distal sheath 58 continues to collapse the strut 64, the support element 31, and the filter element 33 until the distal filter assembly 34 is retrieved and re-collapsed back within distal sheath 58 (not explicitly shown). Any foreign particles trapped within the distal filter element 33 are contained therein as the distal filter assembly 34 is re-sheathed. The distal sheath 58 is then steered into a configuration where the distal sheath 58 is generally parallel with the distal shaft 56. Said differently, the distal sheath 58 is steered such that it has a generally linear orientation. The proximal sheath 44 is then advanced distally relative to proximal filter assembly 36. This causes proximal filter assembly 36 to collapse around the distal shaft 56, trapping any particles within the collapsed proximal filter element 37. The proximal sheath 44 continues to be moved distally towards the distal sheath 58 until the proximal sheath 44 is coupled with or nearly coupled with the distal sheath 58. The entire system 30 can then be removed from the subject.

The second filter system 74 can be removed either before, substantially simultaneously with, or after the first filter system 30. The outer sheath 82 is advanced distally relative to the filter assembly 78. This causes the filter assembly 78 to collapse, trapping any particles within the collapsed filter element 92. The outer sheath 82 continues to be moved distally until the entire filter assembly 78 is within the sheath 82. The entire system 74 can then be removed from the subject.

In any of the embodiments mentioned herein, the filter or filter assemblies 34, 36, 78 may alternatively be detached from the delivery catheter, and the delivery catheter removed leaving the filter assemblies 34, 36, 78 behind. The filter or filter assemblies 34, 36, 78 can be left in place permanently, or retrieved by snaring it with a retrieval catheter following a post procedure treatment period of time. Alternatively, the filter assemblies 34, 36, 78 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 1C:
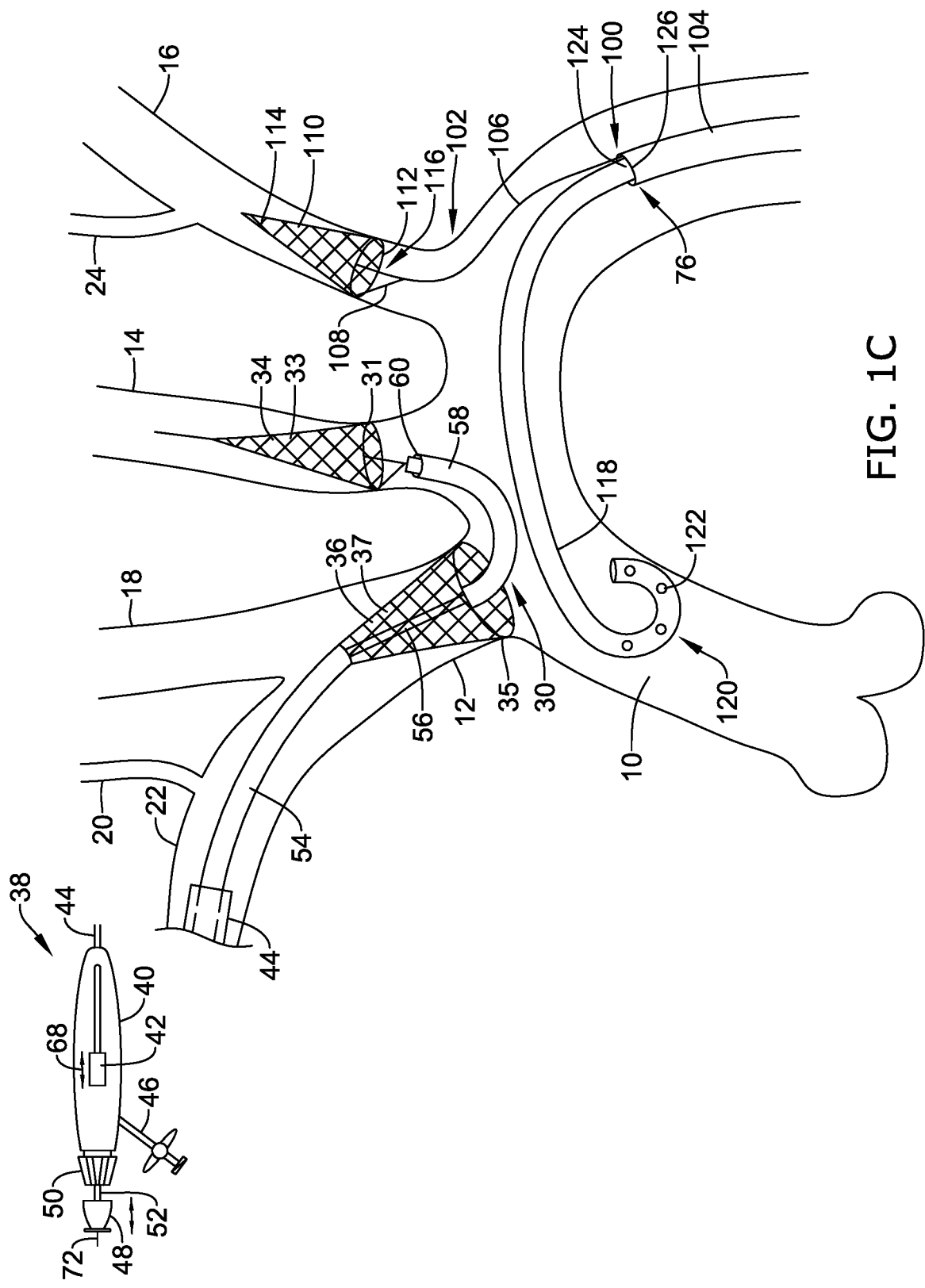
FIG. 1C illustrates an alternate embodiment of the three filter system of FIGS. 1A and 1B.

FIG. 1C illustrates an alternative embodiment for the systems of FIGS. 1A and 1B. In FIG. 1C, the second protection device 100 is configured to be positioned in the left subclavian artery 16. In the illustrative embodiment of FIG. 1C, the first protection system 30 is deployed as described above with respect to FIG. 1A. The second protection device, or filter system, 100 comprises a proximal portion (not explicitly shown) and a distal portion 102. The proximal portion is configured to be held and manipulated by a user such as a surgeon. In some cases, the proximal portion may be coupled to a handle configured to facilitate delivery and deployment of the system 100. In some cases, the handle of the second protection device 100 may be similar in form and function to the handle 40 described herein. The distal portion 102 is configured to be positioned at a target location such as the left subclavian artery 16 or the left vertebral artery 24. When the distal portion 102 is configured to be positioned at the left subclavian artery 16, the location may be upstream of the left vertebral artery 24 such that the blood is filter prior to entering the left vertebral artery 24.

The protection device 100 may include at least an outer sheath 104 and a filter assembly 110. The filter assembly 110 may include a support element or frame 112 and a filter element 114. In some embodiments, the filter assembly 110 may be a stent supported filter. The frame 112 may be similar in form and function to the frames 31, 35 described herein. Similarly, the filter element 114 may be similar in form and function to the filter element 33 described herein. In some embodiments, the filter assembly 110 may be self-expanding. The support element 112 generally provides expansion support to the filter element 114 in its expanded configurations, while the filter element 114 is adapted to filter fluid, such as blood, and trap particles flowing therethrough. The expansion support 112 is adapted to engage the wall of the lumen in which it is expanded. The filter element 114 has pores therein that are sized to allow the blood to flow therethrough, but are small enough to prevent unwanted foreign particles from passing therethrough. The foreign particles are therefore trapped by and within the filter element 114. As shown in FIG. 1C, the filter assembly 110 has a generally proximally-facing opening 116. In other embodiments, the opening 116 may be distally facing. The orientation of the opening 116 may vary depending on where the access incision is located and/or the vessel in which it is deployed.

The outer sheath 104 may define a lumen 124 extending from a proximal end to the distal end 126 thereof. The lumen 124 may be configured to slidably receive the filter assembly 110, a pigtail or angiography catheter 118, and/or a procedural catheter (such as, but not limited to a TAVR or TAVI procedural catheter or device), etc. The pigtail catheter 118 and the filter assembly 110 may be radially inward of the outer sheath 104. In some embodiments, the pigtail catheter 118 and the filter assembly 110 may be advanced simultaneously (or substantially simultaneously) through the lumen 124 of the outer sheath 104. In other embodiments, the pigtail catheter 118 and the filter assembly 110 may be advanced sequentially or one after the other. The filter assembly 110 may be radially within the outer sheath 104 in a delivery state or shape or position. The outer sheath 104 may have a diameter large enough for a procedural catheter to pass therethrough. The outer sheath 104 may comprise an atraumatic distal tip. In some cases, the outer sheath 104 may be flexible and/or atraumatic. The outer sheath 104 may comprise a curvature, for example based on an intended placement location (e.g., the left subclavian artery 16 and/or the aortic arch 10). Alternatively, or additionally, the outer sheath 104 may be steerable.

The filter assembly 110 may be coupled (e.g., crimped, welded, soldered, etc.) to a distal end of a deployment wire or filter wire 106 via a strut or wire 108. When both or all of the filter wire 106 and the strut 108 are provided, the filter wire 106 and the strut 108 may be coupled within the outer sheath 104 proximal to the filter assembly 100 using a crimp mechanism. In other embodiments, the filter wire 106 and the strut 108 may be a single unitary structure. The filter wire 106 and/or strut 108 can comprise a rectangular ribbon, a round (e.g., circular, elliptical) filament, a portion of a hypotube, a braided structure (e.g., as described herein), combinations thereof, and the like. The filter wire 106 can be coupled to a handle or a component thereof (not explicitly shown) to provide differential longitudinal movement relative to the outer sheath 104, which can sheathe and unsheathe the filter assembly 110 from the outer sheath 104.

While not explicitly shown, the filter assembly 110 may, in addition to, or alternatively to, the filter wire 106, be mounted on a tubular shaft. The tubular shaft may be similar in form and function to the guiding member 60 described above and may be advanced within the lumen 124 of the outer sheath 104. It is contemplated that the tubular shaft may be advanced over a guidewire to facilitate navigation to the left subclavian artery 16. For example, the left subclavian artery 16 may be cannulated with a guidewire and the filter assembly 110 inserted into the left subclavian artery 16 by advancing the tubular shaft over the guidewire.

The distal portion 102 may include fluoroscopic markers to aid a user in positioning the device 100, deploying the filter assembly 110, utilizing the pigtail catheter 118, etc. A fluoroscopic marker (not explicitly shown) may be positioned proximate to a distal end of the outer sheath 104. Another fluoroscopic marker (not explicitly shown) may be positioned proximate to a proximal end of the filter assembly 110. In some cases, another fluoroscopic marker (not explicitly shown) may be proximate to a distal end of the filter assembly 110. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

The right femoral artery may be accessed using an introducer. The outer sheath 104 is steered, into or towards the aortic arch 10. In some cases, the outer sheath 104 may be advanced over a guidewire, although this is not required. In some implementations, the guidewire and the outer sheath 104, pigtail catheter 118, and/or filter assembly 110 may be tracked together, with the guidewire leading the outer sheath 104 a (e.g., advance the guidewire a distance, then advance the outer sheath 104 over the guidewire approximately the same distance). In some cases, where the guidewire is floppy or lacks rigidity, it may be introduced inside the outer sheath 104 and then advanced ahead of the filter assembly 110 in the vasculature. The guidewire may be advanced at least about 6 centimeters (cm) distal to the distal end of the filter assembly 110, although this is not required.

The outer sheath 104 may be advanced into the descending portion of the aortic arch 10. The pigtail catheter 118 and filter assembly 110 are then advanced through the outer sheath 104 (if they were not advanced with the outer sheath 104). In some cases, the pigtail catheter 118 and filter assembly 110 may be advanced together while in other cases they may be advanced sequentially (with either the pigtail catheter 118 or the filter assembly 110 leading). The pigtail catheter 118 may be advanced into the ascending portion of the aortic arch 10 where it may deliver a radiopaque fluid or contrast fluid to facilitate visualization of the procedure. A distal end region 120 of pigtail catheter 118 may have a generally arcuate shape (although this is not required) and include one or more apertures 122 therein. The one or more apertures 122 may be in fluid communication with a lumen and may be configured to deliver the radiopaque fluid or contrast fluid. As described above, the filter assembly 110 is attached to a filter wire 106 and is advanced by the user through manipulation of filter wire 106. By manipulating filter wire 106 coupled with optional sporadic injection of contrast media through apertures 122 in the pigtail catheter 118, the user may be able to better cannulate left subclavian artery 16 and deploy filter assembly 110 therein. In some cases, the filter assembly 110 may be maintained in a delivery configuration through a radial force (e.g., by the outer sheath 104 or a tubular shaft) and expand upon distal actuation. In other embodiments, the user may exert a force on the filter assembly 110 (e.g., through the filter wire 106) to deploy the filter assembly 110. Having now placed the filter assembly 110, the entire cerebral vasculature is now protected.

Tracking of the protection device 100 may be performed under fluoroscopy, for example using radiopaque markers (e.g., at a distal end of the outer sheath 104 and/or the filter assembly 110) and/or radiopaque fluid or contrast media. Radiopaque fluid may be provided through the pigtail catheter 118 and/or the outer sheath 104. The protection device 100 may be positioned so that the filter assembly 110 is upstream of the left vertebral artery 24 or proximate to the ostium of the left subclavian artery 16 so that the filter assembly 110 can inhibit or prevent embolic material from entering the cerebral vasculature through the left vertebral artery 24. However, it is contemplated that positioning may be based on available anatomy.

During navigation through the vasculature, the filter assembly 110 may be disposed within a lumen of the outer sheath 104 and held in a collapsed position therein until the filter assembly 110 advanced distally from the outer sheath 104 and/or the outer sheath 104 is proximally retracted relative to the filter assembly 110. After the pigtail catheter 118 has been deployed, the outer sheath 104 may then be proximally retracted (and/or the filter wire 106 distally advanced) to deploy the filter assembly 110. In some cases, the filter assembly 110 may be deployed before advancing the pigtail catheter 118, or substantially simultaneously therewith. The filter assembly 110 may be positioned to direct any dislodged debris downstream away from the left subclavian artery 16 and the left vertebral artery 24.

Once the protection device 100 is in position, the filter assembly 110 may be deployed from the outer sheath 104. For example, the outer sheath 104 may be proximally retracted and/or the filter assembly 110 may be distally advanced. Radiopaque markers, for example on the filter assembly 110 can help determine when the filter assembly 110 achieves a deployed state. Differential longitudinal movement of the filter assembly 100 and the outer sheath 104 can cease upon full or appropriate deployment of the filter assembly 110. Apposition of the filter assembly 110 with sidewalls of the left subclavian artery 16 can be verified, for example using radiopaque fluid or contrast media. Radiopaque fluid may be provided through the pigtail catheter 118 and/or the outer sheath 104. If the radiopaque fluid is able to flow between the frame of the filter assembly 110 and the sidewalls of the left subclavian artery 16, then the filter assembly 110 may be improperly positioned (e.g., indicative of inadequate deployment, inadequate sizing, calcium, etc.). The filter assembly 110 may be retracted back into the outer sheath 104 and redeployed, or a different protection device may be used. After positioning of the protection device 100, the pigtail catheter 118 may be withdrawn and the procedural catheter advanced through the lumen 124 of the outer sheath 104. Together, the first protection device 30 and the second protection device 100 may protect all four cerebral arteries 14, 18, 20, 24 during a procedure.

The protection device(s) 30, 100 can thereafter be removed from the subject (or at any point in the procedure). In an exemplary embodiment, the distal filter assembly 34 is first retrieved back within distal sheath 58 to the collapsed configuration. To do this, the guiding member 60 is retracted proximally relative to the distal sheath 58. This relative axial movement causes the distal sheath 58 to engage a strut or wire 64 and begin to move strut 64 towards guiding member 60. The support element 31, which is coupled to the strut 64, begins to collapse upon the collapse of the strut 64. The filter element 33 therefore begins to collapse as well. Continued relative axial movement between the guiding member 60 and the distal sheath 58 continues to collapse the strut 64, the support element 31, and the filter element 33 until the distal filter assembly 34 is retrieved and re-collapsed back within distal sheath 58 (not explicitly shown). Any foreign particles trapped within the distal filter element 33 are contained therein as the distal filter assembly 34 is re-sheathed. The distal sheath 58 is then steered into a configuration where the distal sheath 58 is generally parallel with the distal shaft 56. Said differently, the distal sheath 58 is steered such that it has a generally linear orientation. The proximal sheath 44 is then advanced distally relative to proximal filter assembly 36. This causes proximal filter assembly 36 to collapse around the distal shaft 56, trapping any particles within the collapsed proximal filter element 37. The proximal sheath 44 continues to be moved distally towards the distal sheath 58 until the proximal sheath 44 is coupled with or nearly coupled with the distal sheath 58. The entire system 30 can then be removed from the subject.

The second filter system 100 can be removed either before, substantially simultaneously with, or after the first filter system 30. The outer sheath 104 is advanced distally relative to the filter assembly 110. This causes the filter assembly 110 to collapse, trapping any particles within the collapsed filter element 114. The outer sheath 104 continues to be moved distally until the entire filter assembly 110 is within the sheath 104. The entire system 100 can then be removed from the subject.

In any of the embodiments mentioned herein, the filter or filter assemblies 34, 36, 110 may alternatively be detached from the delivery catheter, and the delivery catheter removed leaving the filter assemblies 34, 36, 110 behind. The filter or filter assemblies 34, 36, 110 can be left in place permanently, or retrieved by snaring it with a retrieval catheter following a post procedure treatment period of time. Alternatively, the filter assemblies 34, 36, 110 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 1D:
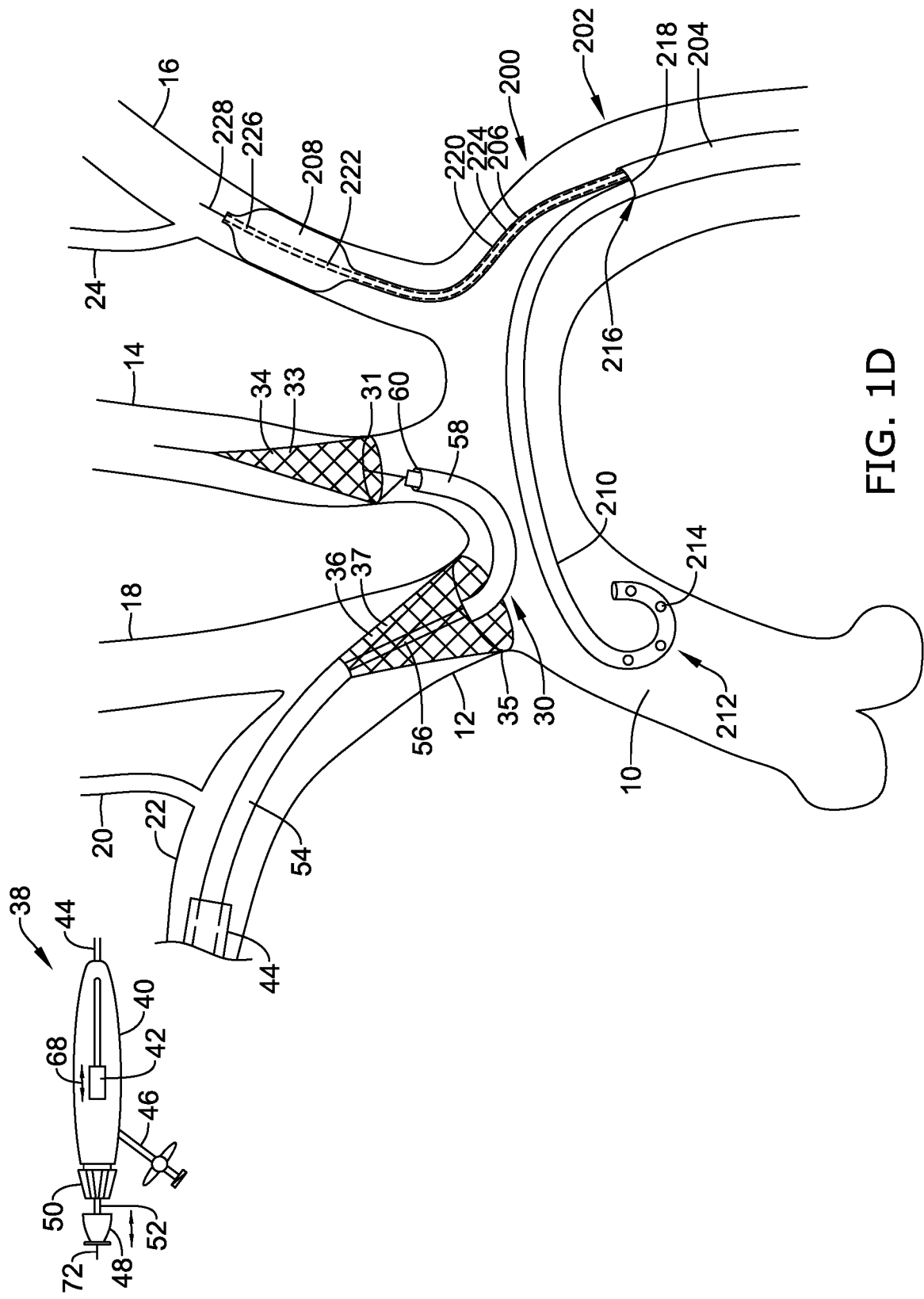
FIG. 1D illustrates an alternate embodiment of the three filter system of FIGS. 1A and 1B.

FIG. 1D illustrates another alternative embodiment for the systems of FIGS. 1A and 1B. In FIG. 1D, the second protection device 200 is configured to be positioned in the left subclavian artery 16. In the illustrative embodiment of FIG. 1D, the first protection system 30 is deployed as described above with respect to FIG. 1A. The second protection device, or deflection system, 200 comprises a proximal portion (not explicitly shown) and a distal portion 202. The proximal portion is configured to be held and manipulated by a user such as a surgeon. In some cases, the proximal portion may be coupled to a handle configured to facilitate delivery and deployment of the system 200. In some cases, the handle of the second protection device 200 may be similar in form and function to the handle 40 described herein. The distal portion 202 is configured to be positioned at a target location such as the left subclavian artery 16 or the left vertebral artery 24. When the distal portion 202 is configured to be positioned at the left subclavian artery 16, the location may be upstream of the left vertebral artery 24 such that the blood flow is blocked prior to entering the left vertebral artery 24.

The protection device 200 may include at least an outer sheath 204 and an expandable or inflatable balloon 208. The balloon 208 may be coupled to a catheter shaft 206. The balloon 208 may be made from materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyether-ester, polyester, polyamide, elastomeric polyamides, polyether block amide (PEBA), as well as other suitable materials, or mixtures, combinations, copolymers thereof, polymer/metal composites, and the like. In some instances, the balloon 208 may include a single layer of material, whereas in other instances the balloon 208 may be of a multi-layer construction, including a plurality of layers of materials. For instance, the balloon 208 may be formed as a co-extrusion or tri-layer extrusion in some instances.

The shaft 206 may be a catheter shaft, similar to typical catheter shafts. For example, the catheter shaft 206 may include an outer tubular member 220 and an inner tubular member 222 extending through at least a portion of the outer tubular member 220. The tubular members 220, 222 may be manufactured from a number of different materials. For example, the tubular members may be made of metals, metal alloys, polymers, metal-polymer composites or any other suitable materials.

The tubular members 220, 222 may be arranged in any appropriate way. For example, in some embodiments the inner tubular member 222 can be disposed coaxially within a lumen 224 of the outer tubular member 220. According to these embodiments, the inner and outer tubular members 222, 220 may or may not be secured to one another along the general longitudinal axis of the catheter shaft 206. Alternatively, the inner tubular member 222 may follow the inner wall or otherwise be disposed adjacent the inner wall of the outer tubular member 220. In other embodiments, the tubular members 220, 222 may be arranged in another desired fashion.

The inner tubular member 222 may include an inner lumen 226. In at least some embodiments, the inner lumen 226 is a guidewire lumen for receiving the guidewire 228 therethrough. Accordingly, the catheter 206 can be advanced over the guidewire 228 to the desired location. The guidewire lumen 226 may extend along essentially the entire length of the catheter shaft 206 such that catheter resembles traditional "over-the-wire" catheters. Alternatively, the guidewire lumen 226 may extend along only a portion of the catheter shaft 206 such that the catheter resembles "single-operator-exchange" or "rapid-exchange" catheters.

The catheter shaft 206 may also include an inflation lumen 224 that may be used, for example, to transport inflation media to and from the balloon 208 to selectively inflate and/or deflate the balloon 208. The location and position of the inflation lumen 224 may vary, depending on the configuration of the tubular members 220, 222. For example, when the outer tubular member 220 surrounds the inner tubular member 222, the inflation lumen 224 may be defined within the space between the tubular members 220, 222. In embodiments in which the outer tubular member 220 is disposed alongside the inner tubular member 222, then the inflation lumen 224 may be the lumen of the outer tubular member 220.

The balloon 208 may be coupled to the catheter shaft 206 in any of a number of suitable ways. For example, the balloon 208 may be adhesively or thermally bonded to the catheter shaft 206. In some embodiments, a proximal waist of the balloon 208 may be bonded to the catheter shaft 206, for example, bonded to the distal end of the outer tubular member 220, and a distal waist of the balloon 208 may be bonded to the catheter shaft 206, for example, bonded to the distal end of the inner tubular member 222. The exact bonding positions, however, may vary.

The outer sheath 204 may define a lumen 216 extending from a proximal end to the distal end 218 thereof. The lumen 216 may be configured to slidably receive the catheter 206 and balloon 208, a pigtail or angiography catheter 210, and/or a TAVR procedural catheter (or another procedural catheter or device), etc. The pigtail catheter 210 and the catheter 206 may be radially inward of the outer sheath 204. In some embodiments, the pigtail catheter 210 and the catheter 206 may be advanced simultaneously (or substantially simultaneously) through the lumen 216 of the outer sheath 204. In other embodiments, the pigtail catheter 210 and the catheter 206 may be advanced sequentially or one after the other. The catheter 206 may be radially between the outer sheath 204 in a delivery state or position (e.g., with the balloon 208 in a collapsed or uninflated state). The outer sheath 204 may have a diameter large enough for a procedural catheter to pass therethrough. The outer sheath 204 may comprise an atraumatic distal tip. In some cases, the outer sheath 204 may be flexible and/or atraumatic. The outer sheath 204 may comprise a curvature, for example based on an intended placement location (e.g., the left subclavian artery 16 and/or the aortic arch 10). Alternatively, or additionally, the outer sheath 204 may be steerable.

The distal portion 202 may include fluoroscopic markers to aid a user in positioning the device 200, deploying the balloon 208, utilizing the pigtail catheter 210, etc. A fluoroscopic marker (not explicitly shown) may be positioned proximate to a distal end of the outer sheath 204. Another fluoroscopic marker (not explicitly shown) may be positioned proximate to a proximal end of the balloon 208. In some cases, another fluoroscopic marker (not explicitly shown) may be proximate to a distal end of the balloon 208. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

The right femoral artery may be accessed using an introducer. The outer sheath 204 is steered, into or towards the aortic arch 10. In some cases, the outer sheath 204 may be advanced over a guidewire, although this is not required. In some implementations, the guidewire and the outer sheath 204, pigtail catheter 210, and/or catheter 206 may be tracked together, with the guidewire leading the outer sheath 204 (e.g., advance the guidewire a distance, then advance the outer sheath 204 over the guidewire approximately the same distance). In some cases, where the guidewire is floppy or lacks rigidity, it may be introduced inside the outer sheath 204 and then advanced ahead of the balloon 208 in the vasculature. The guidewire may be advanced at least about 6 centimeters (cm) distal to the distal end of the balloon 208, although this is not required.

The outer sheath 204 may be advanced into the descending portion of the aortic arch 10. The pigtail catheter 210 and catheter 206 are then advanced through the outer sheath 204 (if they were not advanced with the outer sheath 204). In some cases, the pigtail catheter 210 and catheter 206 may be advanced together while in other cases they may be advanced sequentially (with either the pigtail catheter 210 or the catheter 206 leading). The pigtail catheter 210 may be advanced into the ascending portion of the aortic arch 10 where it may deliver a radiopaque fluid or contrast fluid to facilitate visualization of the procedure. A distal end region 212 of pigtail catheter 210 may have a generally arcuate shape (although this is not required) and include one or more apertures 214 therein. The one or more apertures 214 may be in fluid communication with a lumen and may be configured to deliver the radiopaque fluid or contrast fluid.

In some cases, the left subclavian artery 16 may first be cannulated by a guidewire 228, although this is not required. The catheter 206 and balloon 208 may then be advanced into the left subclavian artery 16. Once the balloon 208 is advanced into the left subclavian artery 16, the balloon 208 is inflated by injecting an inflation fluid, such as, but not limited to, saline, saline mixed with a contrast agent, or any other suitable fluid, through the inflation lumen 224 until the balloon 208 occludes the left subclavian artery 16. This may prevent blood flow through the left subclavian artery 16 and thus blood flow through the left vertebral artery 24. Having now placed the balloon 208, the entire cerebral vasculature is now protected.

Tracking of the protection device 200 may be performed under fluoroscopy, for example using radiopaque markers (e.g., at a distal end of the outer sheath 204, the catheter 206, and/or the balloon 208) and/or radiopaque fluid or contrast media. Radiopaque fluid may be provided through the pigtail catheter 210 and/or the outer sheath 204. The protection device 200 may be positioned so that the balloon 208 is upstream of the left vertebral artery 24 or proximate to the ostium of the left subclavian artery 16 so that the balloon 208 can block blood flow, and thus inhibit or prevent embolic material from entering the cerebral vasculature through the left vertebral artery 24. However, it is contemplated that positioning may be based on available anatomy.

During navigation through the vasculature, the balloon 208 may be disposed within a lumen of the outer sheath 204 and maintained in an uninflated configuration until the balloon 208 advanced distally from the outer sheath 204 and/or the outer sheath 204 is proximally retracted relative to the balloon 208. After the pigtail catheter 210 has been deployed, the outer sheath 204 may then be proximally retracted (and/or the catheter 206 distally advanced) to deploy the balloon 208. In some cases, the balloon 208 may be deployed before advancing the pigtail catheter 210, or substantially simultaneously therewith.

Radiopaque markers, for example on the balloon 208 can help determine when the balloon 208 achieves a deployed state. Apposition of the balloon 208 with sidewalls of the left subclavian artery 16 can be verified, for example using radiopaque fluid or contrast media. Radiopaque fluid may be provided through the pigtail catheter 210 and/or the outer sheath 204. If the radiopaque fluid is able to flow between the balloon 208 and the sidewalls of the left subclavian artery 16, then the balloon 208 may be improperly positioned (e.g., indicative of inadequate deployment, inadequate sizing, calcium, etc.). The balloon 208 may be partially deflated and repositioned. In other embodiments, more inflation fluid may be provided to the balloon 208. After positioning of the protection device 200, the pigtail catheter 210 may be withdrawn and the procedural catheter advanced through the lumen 216 of the outer sheath 204. Together, the first protection device 30 and the second protection device 200 may protect all four cerebral arteries 14, 18, 20, 24 during a procedure.

The protection device(s) 30, 200 can thereafter be removed from the subject (or at any point in the procedure). The first protection device 30 can be removed as described herein with respect to FIG. 1B. The second system 200 can be removed either before, substantially simultaneously with, or after the first filter system 30. The inflation fluid may be removed from the balloon 208 to collapse the balloon 208. The outer sheath 204 is advanced distally relative to the balloon 208 and/or the catheter 206 is proximally retracted to draw the balloon 208 into the lumen 216 of the outer sheath 204. The entire system 200 can then be removed from the subject.

Figure 2:
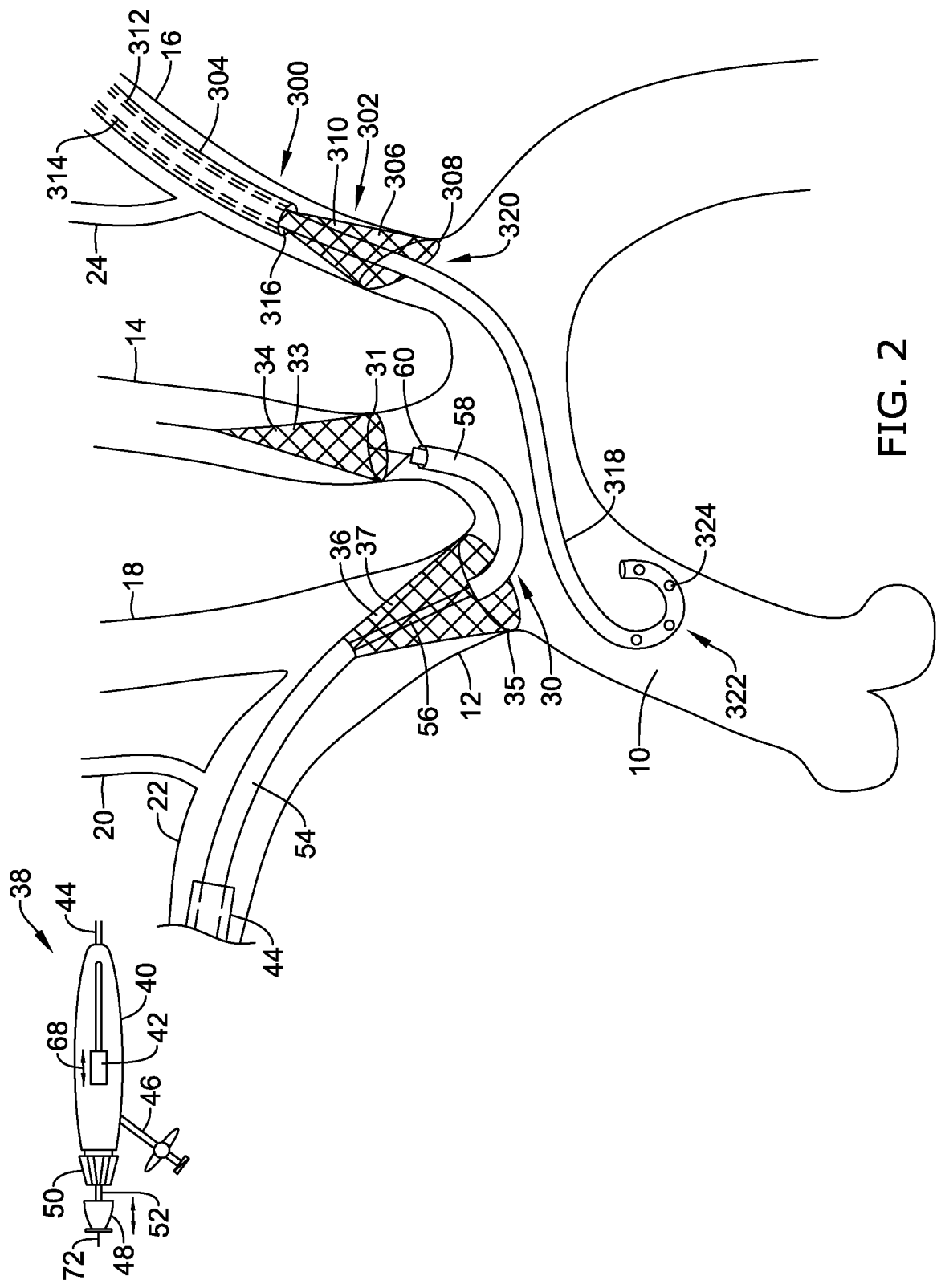
FIG. 2 illustrates another embodiment of a three filter system.

FIG. 2 illustrates another illustrative protection device 300, or filter system to be used with the filter system 30 of FIG. 1A. In FIG. 2, the second protection device 300 is configured to be positioned in the left subclavian artery 16. In the illustrative embodiment of FIG. 2, the first protection system 30 is deployed as described above with respect to FIG. 1A. After the first filter system 30 has been positioned (or substantially simultaneously therewith or prior to implantation of the first system 30), a second protection device or filter system 300 may be deployed, as shown in FIG. 2. In some embodiments, the second filter system 300 may be positioned within the left subclavian artery 16, although this is not required.

The protection device, or filter system, 300 comprises a proximal portion (not explicitly shown) and a distal portion 302 including a filter assembly 306. The proximal portion may be coupled to a handle (not explicitly shown) configured to remain outside the body. In some cases, the handle of the second protection device 300 may be similar in form and function to the handle 40 described herein. The proximal portion is configured to be held and manipulated by a user such as a surgeon. The distal portion 302 is configured to be positioned at a target location such as the left subclavian artery 16. When the distal portion 302 is configured to be positioned within the aortic arch 10, the location may be upstream of the left subclavian artery 16 such that the blood is filtered prior to entering the left subclavian artery 16 and hence the left vertebral artery 24. The distal portion 302 may include outer sheath 304 and an inner tubular member 312 coupled to the filter assembly 306. The inner tubular member 312 may define a lumen 314 extending from a proximal end (not explicitly shown) to the distal end 316 thereof. The lumen 314 may be configured to receive other medical devices, including, but not limited to an angiography or pigtail catheter 318, a TAVR procedural catheter (or another procedural catheter or device), etc. The pigtail catheter 318 may be radially inward of the inner tubular member 312 and the inner tubular member 312 may be radially inward of the outer sheath 304. The filter assembly 306 may be radially between the outer sheath 304 and the pigtail catheter 318 (e.g., radially inward of the outer sheath 304 and the pigtail catheter 318 radially inward of the filter assembly 306) in a delivery state or position. While not explicitly shown, the second protection device 300 may include a filter wire (not explicitly shown) or a guidewire radially inward of the inner tubular member 312 and/or the pigtail catheter 318. The outer sheath 304 and/or the inner tubular member 312 may have a diameter large enough for a procedural catheter to pass therethrough. The outer sheath 304 may comprise an atraumatic distal tip. Other features of the protection device 300 and other protection devices described herein may be flexible and/or atraumatic. The outer sheath 304 may comprise a curvature, for example based on an intended placement location (e.g., the left subclavian artery 16).

The handle (not explicitly shown) can be used to translate the outer sheath 304 and/or a filter assembly 306 (e.g., coupled to the inner tubular member 312). For example, the handle may include a mechanism to proximally retract the outer sheath 304, distally advance the filter assembly 306 out of the outer sheath 304, or both proximally retract the outer sheath 304 and distally advance the filter assembly 306 (e.g., simultaneously or serially), which can allow the filter assembly 306 to radially expand. The handle may also be configured to have an opposite translation effect, which can allow the filter assembly 306 to be radially collapsed (e.g., due to compression by the outer sheath 304) as the filter assembly 306 is drawn into the outer sheath 304. Other deployment systems are also possible, for example comprising gears or other features such as helical tracks (e.g., configured to compensate for any differential lengthening due to foreshortening of the filter assembly 306, configured to convert rotational motion into longitudinal motion), a mechanical element, a pneumatic element, a hydraulic element, etc. for opening and/or closing the filter assembly 306.

The filter assembly 306 may include a support element or frame 308 and a filter element 310. In some embodiments, the filter assembly 306 may be a stent supported filter. The frame 308 may generally provide expansion support to the filter element 310 in the expanded state. The frame 308 may be similar in form and function to the frames 31, 35 described herein. Similarly, the filter element 310 may be similar in form and function to the filter elements 33, 37 described herein. The support element 308 generally provides expansion support to the filter element 310 in its expanded configurations, while the filter element 310 is adapted to filter fluid, such as blood, and trap particles flowing therethrough. The expansion support 308 is adapted to engage the wall of the lumen in which it is expanded. The filter element 310 has pores therein that are sized to allow the blood to flow therethrough, but are small enough to prevent unwanted foreign particles from passing therethrough. The foreign particles are therefore trapped by and within the filter element 310. It is contemplated that the filter assembly 306 may have one or more openings configured to allow another device (such as the pigtail catheter 318 or a procedural catheter) to pass therethrough. In some embodiments, the filter assembly 306 and/or the inner tubular member 312 may be replaced with a balloon catheter, such as the balloon catheter 206 described herein. It is contemplated that the pigtail catheter 318 may be placed through the center of the balloon through a lumen that is distinct from the balloon inflation lumen, or the pigtail catheter 318 may be placed through the balloon inflation lumen that incorporates a seal with the exterior surface of the pigtail catheter to prevent leakage of the inflation fluid.

As shown in FIG. 2, the filter assembly 306 has a generally distally-facing opening 320. In other embodiments, the opening 320 may be proximally facing. The orientation of the opening 320 may vary depending on where the access incision is located and/or the vessel in which it is deployed.

The distal portion 302 may include fluoroscopic markers to aid a user in positioning the device 300, deploying the filter assembly 306, utilizing the pigtail catheter 318, etc. A fluoroscopic marker (not explicitly shown) may be positioned proximate to a distal end of the outer sheath 304. Another fluoroscopic marker (not explicitly shown) may be positioned proximate to a proximal end of the filter assembly 306. In some cases, another fluoroscopic marker (not explicitly shown) may be proximate to a distal end of the filter assembly 306. Another fluoroscopic marker (not explicitly shown) may be proximate to a distal end of the inner member 312. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some embodiments, the protection device 300 may include a guidewire (not explicitly shown) extending therethrough, although the guidewire may be characterized as being separate from the protection device 300, for example independently sold, packaged, and/or directed. The guidewire may extend through a lumen of the outer sheath 304, the inner tubular member 312 and/or the pigtail catheter 318. The lumen of the outer sheath 304, the inner tubular member 312 and/or the pigtail catheter 318 may be configured to receive a guidewire having a diameter between about 0.014 inches (0.356 mm) and about 0.025 inches (0.635 mm). If so provided, the guidewire may extend through a lumen of the filter assembly 306. For example, any portion of the protection device 300 may be tracked over the guidewire to position the protection device 300 at a desired location.

The filter assembly 306 may be positioned, for example, in the left subclavian artery 16, to protect the cerebral vasculature (e.g., the left vertebral artery 24) from embolic debris during an endovascular procedure such as TAVI. While the procedure is described as positioning the second filter assembly 306 in the left subclavian artery 16, the method is not limited to positioning the second filter assembly 306 within the left subclavian artery 16. The second filter assembly 306 may be positioned within other arteries (or other lumens), as desired, such as, but not limited to the aortic arch 10 or the left vertebral artery 24. The filter assembly 306 may be positioned in the left subclavian artery 16 upstream of the left vertebral artery 24. The user may choose a protection device 300 comprising a distal-facing filter assembly 306 having a diameter appropriate for the artery (or another lumen) in which it is to be deployed. The protection device 300 may be packaged in a sterile coiled packaging. The outer sheath 304 may include a curvature, for example complementing the size and orientation of the filter assembly 306. The outer sheath 304 and/or the inner tubular member 312 may be steerable (e.g., a pull wire-controlled sheath).

Lumens of the protection device 300, for example a lumen of the outer sheath 304, a lumen 314 of the inner member 312, and/or a lumen of the pigtail catheter 318, may be flushed (e.g., using saline) once or several times before, during, and/or after the procedure. The filter assembly 306 of the protection device 300 may be flushed and/or submerged (e.g., in a bowl of saline). Flushing and/or submerging of the filter assembly 306 may be with the filter assembly 306 in the outer sheath 304 (e.g., in the compressed state) and/or with the filter assembly 306 out of the outer sheath 304 (e.g., in the deployed state). If the filter assembly 306 is flushed and/or submerged in the deployed state, the filter assembly 306 may be compressed into the outer sheath 304 before use.

The left brachial artery or the left radial artery may be accessed using an introducer. The outer sheath 304 is steered, into or towards the left subclavian artery 16. In some cases, the outer sheath 304 may be advanced over a guidewire, although this is not required. In some implementations, the guidewire and the outer sheath 304 and/or filter assembly 306 may be tracked together, with the guidewire leading the outer sheath 304 and/or filter assembly 306 (e.g., advance the guidewire a distance, then advance the outer sheath 304 and/or the filter assembly 306 over the guidewire approximately the same distance). In some cases, where the guidewire is floppy or lacks rigidity, it may be introduced inside the outer sheath 304 and then advanced ahead of the device 300 in the vasculature. The guidewire may be advanced at least about 6 centimeters (cm) distal to the distal end of the filter assembly 306, although this is not required.

The outer sheath 304 may be curved and/or steerable to facilitate navigation from the femoral artery to the left subclavian artery 16. The inner tubular member 312 may be advanced simultaneously with or serially to the outer sheath 304. Additionally, the pigtail catheter 318 may be advanced simultaneously with or serially to the inner tubular member 312 and/or the outer sheath 304. Once the outer sheath 304 is positioned in the left subclavian artery 16 (distal to the ostium of the left vertebral artery 24), the pigtail catheter 318 may be advanced distally from the outer sheath 304. A distal end region 322 of pigtail catheter 318 may have a generally arcuate shape (although this is not required) and may include one or more apertures 324 therein. The one or more apertures 324 may be in fluid communication with a lumen and may be configured to deliver a radiopaque fluid or contrast fluid.

Tracking of the protection device 300 may be performed under fluoroscopy, for example using radiopaque markers (e.g., at a distal end of the outer sheath 304 and/or the inner tubular member 312) and/or radiopaque fluid or contrast media. Radiopaque fluid may be provided through the inner tubular member 312, the pigtail catheter 318, and/or the outer sheath 304. The protection device 300 may be positioned so that the filter assembly 306 is upstream of the left vertebral artery 24 or proximate to the ostium of the left subclavian artery 16 so that the filter assembly 306 can inhibit or prevent embolic material from entering the cerebral vasculature through the left vertebral artery 24. However, it is contemplated that positioning may be based on available anatomy.

During navigation through the vasculature, the filter assembly 306 may be disposed within a lumen of the outer sheath 304 and held in a collapsed position therein until the filter assembly 306 is advanced distally from the outer sheath 304 and/or the outer sheath 304 is proximally retracted relative to the filter assembly 306. After the pigtail catheter 318 has been deployed, the outer sheath 304 may then be proximally retracted (and/or the inner tubular member 312 distally advanced) to deploy the filter assembly 306. In some cases, the filter assembly 306 may be deployed before advancing the pigtail catheter 318, or substantially simultaneously therewith. The filter assembly 306 may be positioned to capture any dislodged debris prior to entering the left vertebral artery 24.

Once the protection device 300 is in position, the filter assembly 306 may be deployed from the outer sheath 304. For example, the outer sheath 304 may be proximally retracted and/or the filter assembly 306 may be distally advanced. Radiopaque markers, for example on the filter assembly 306 can help determine when the filter assembly 306 achieves a deployed state. Differential longitudinal movement of the filter assembly 306 and the outer sheath 304 can cease upon full or appropriate deployment of the filter assembly 306. Apposition of the filter assembly 306 with sidewalls of the left subclavian artery 16 can be verified, for example using radiopaque fluid or contrast media. Radiopaque fluid may be provided through the pigtail catheter 318, the inner tubular member 312, and/or the outer sheath 304. If the radiopaque fluid is able to flow between the frame of the filter assembly 306 and the sidewalls of the aortic arch, then the filter assembly 306 may be improperly positioned (e.g., indicative of inadequate deployment, inadequate sizing, calcium, etc.). The filter assembly 306 may be retracted back into the outer sheath 304 and redeployed, or a different protection device may be used. After positioning of the protection device 300, the pigtail catheter 318 may be withdrawn and the procedural catheter advanced through the lumen of the inner tubular member 312 and the filter assembly 306. Together, the first protection device 30 and the second protection device 300 may protect all four cerebral arteries 14, 18, 20, 24 during a procedure.

The protection device(s) 30, 300 can thereafter be removed from the subject (or at any point in the procedure). The first protection device 30 can be removed as described herein with respect to FIG. 1B. The second filter system 300 can be removed either before, substantially simultaneously with, or after the first filter system 30. The outer sheath 304 is advanced distally relative to the filter assembly 306. This causes the filter assembly 306 to collapse, trapping any particles within the collapsed filter element 310. The outer sheath 304 continues to be moved distally until the entire filter assembly 306 is within the sheath 304. The entire system 300 can then be removed from the subject.

In any of the embodiments mentioned herein, the filter or filter assemblies 34, 36, 306 may alternatively be detached from the delivery catheter, and the delivery catheter removed leaving the filter assemblies 34, 36, 306 behind. The filter or filter assemblies 34, 36, 306 can be left in place permanently, or retrieved by snaring it with a retrieval catheter following a post procedure treatment period of time. Alternatively, the filter assemblies 34, 36, 306 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 3:
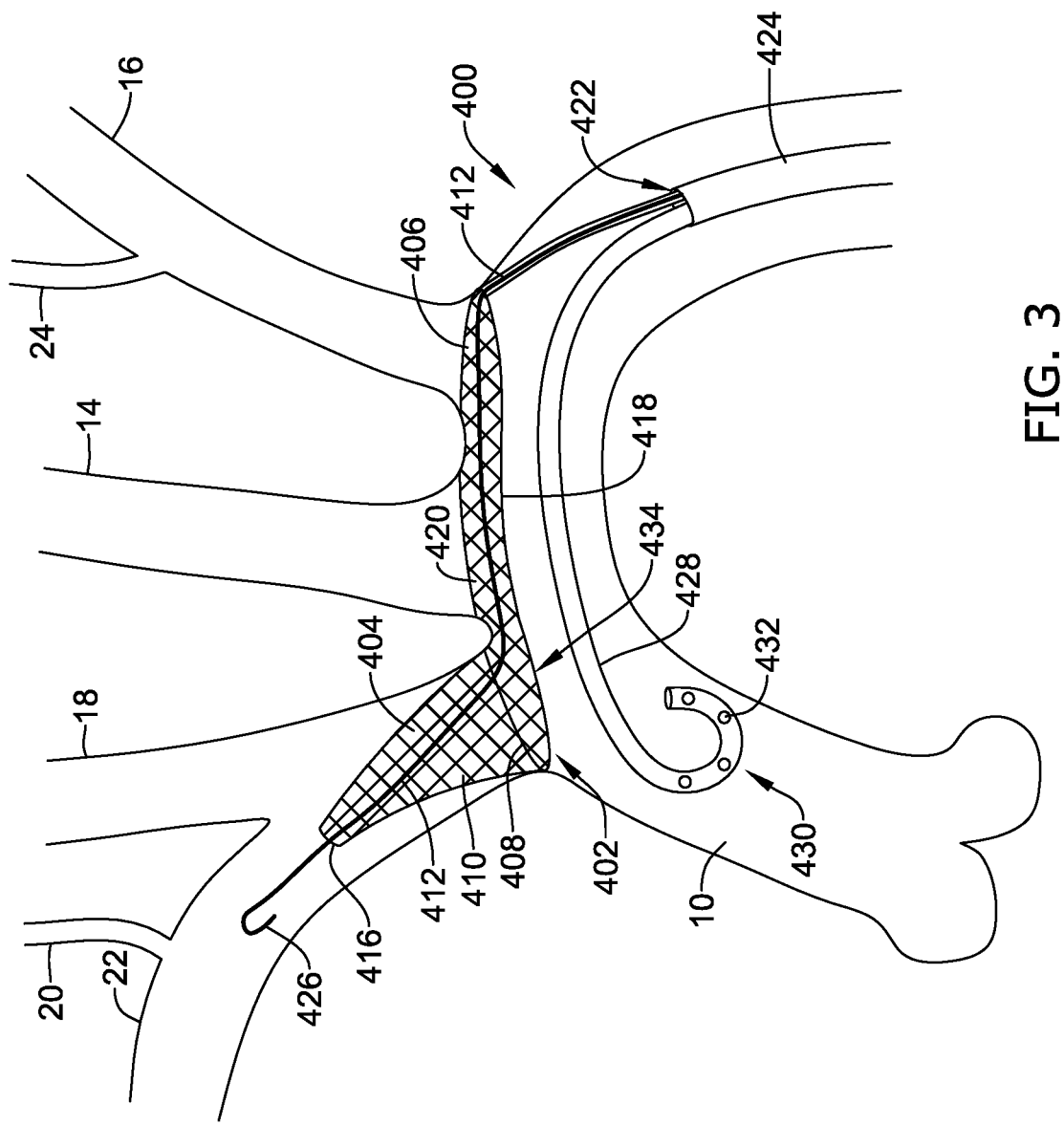
FIG. 3 illustrates a single filter system including a deflector.

FIG. 3 illustrates another illustrative protection device 400, or filter system in which a single filter assembly 402 is configured to protect all four cerebral arteries 14, 18, 20, 24. The filter assembly 402 may include a conical filter region 404 and a deflector 406. In some embodiments, the conical filter region 404 may be configured to be positioned with the innominate artery 12 while the deflector 406 may be positioned over the ostia of the left common carotid artery 14 and the left subclavian artery 16. However, other configurations are also contemplated. For example, the conical filter region 404 may be positioned in the left common carotid artery 14 and the deflector 406 may be positioned over the ostia of the innominate artery 12 and the left subclavian artery 16. In another example, the conical filter region 404 may be positioned in the left subclavian artery 16 and the deflector 406 may be positioned over the ostia of the innominate artery 12 and the left common carotid artery 14.

The conical filter region 404 may include an expandable frame 408 (which may be similar in form and function to the support members 31, 35 described herein), a porous filter material 410 (which may be similar in form and function to the filter elements 33, 37 described herein), and one or more filter wires 412. In some embodiments, the filter wire 412 may be coupled to a distal end 414 of the conical filter region 404, although this is not required. The filter wire 412 may be coupled to the conical filter region 404 at any location desired. As shown in FIG. 3, the conical filter region 404 has a generally proximally-facing opening 434. In other embodiments, the opening 434 may be distally facing. The orientation of the opening 434 may vary depending on where the access incision is located and/or the vessel in which it is deployed.

The deflector 406 may include an expandable frame 418 (which may be similar in form and function to the support members 31, 35 described herein) and a porous filter material 420 (which may be similar in form and function to the filter elements 33, 37 described herein). It is contemplated that the deflector 406 may not include an expandable frame 418, but rather rely on the frame 408 of the conical filter region 404 and/or the blood flow to position the deflector 406. For example, the expandable frame 408 of the conical filter region 404 may act as an anchor for the deflector 406. Regardless of whether an expandable frame 418 is provided, the deflector 406 may be coupled or linked to the expandable frame 408 of the conical filter region 404.

The filter wire 412 may be used to help position and/or maintain the conical filter region 404 at the desired target location. The filter wire 412 may be configured to extend through a lumen 422 of a catheter or delivery sheath 424 to a point outside the body where the filter wire 412 can be manipulated by a user. In some embodiments, the filter assembly 402 may also include one or more pull wires which may be actuated to exert a force on one or both of the frames 408, 418 to help conform the filter assembly 402 to the upper curve of the aortic arch 10. In this manner, not only are all cerebral arteries 14, 18, 20, 24 protected but the filter assembly 402 may not interfere with medical devices, catheters, etc., being passed through the aortic arch 10.

The lumen 422 of the delivery sheath 424 may be configured to receive other medical devices, including, but not limited to an angiography or pigtail catheter 428, a TAVR procedural catheter (or another procedural catheter or device), etc. The filter assembly 402 and the pigtail catheter 428 may be radially inward of the delivery sheath 424. The delivery sheath 424 may have a diameter large enough for a procedural catheter to pass therethrough. The delivery sheath 424 may comprise an atraumatic distal tip. The protection device 400 and other protection devices described herein may be flexible and/or atraumatic. The delivery sheath 424 may comprise a curvature, for example based on an intended placement location (e.g., the innominate artery 12 and/or the aortic arch 10). While not explicitly shown, a handle may be coupled to a proximal end region of the protection system 400 and may be articulated to facilitate deployment of the filter assembly 402 and/or navigation of the delivery sheath 424.

The system 400 is advanced into the subject's right femoral artery through an incision in the right leg. The system 400 may be advanced over or in conjunction with one or more guidewires 426. The delivery sheath 424 may be advanced through the aortic arch 10 until it cannulates the innominate artery 12. The delivery sheath 424 may be curved and/or steerable to facilitate navigation from the femoral artery to the innominate artery 12. During navigation, the filter assembly 402 may be held in a collapsed configuration within the lumen 422 of the delivery sheath 424. When the outer sheath 424 is at or adjacent to the target deployment region, the outer sheath 424 may then be proximally withdrawn to deploy the conical filter region 404. It is contemplated that the user may grasp a proximal end of the filter wire 412 to maintain the conical filter region 404 in the desired configuration as the delivery sheath 424 is withdrawn. As the delivery sheath 424 is further withdrawn, the deflector 406 is exposed and deployed across the ostia of the left common carotid artery 14 and the left subclavian artery 16. In some embodiments, the pigtail catheter 428 could be advanced distally of the delivery sheath 424 the aortic arch 10 prior to deploying filter assembly 402 to assist in the visualization and placement of the filter assembly 402. For example, a distal end region 430 of the pigtail catheter 428 may have a generally arcuate shape (although this is not required) and may include one or more apertures 432 therein. The one or more apertures 432 may be in fluid communication with a lumen and may be configured to deliver a radiopaque fluid or contrast fluid. It is further contemplated that one or more radiopaque makers may be provided on any portion of the system 400 to facilitate visualization.

As can be seen in FIG. 3, the protection system 400 traps (and/or deflects) foreign particles and prevents them from traveling into the four arteries 14, 18, 20, 24 that carry oxygenated blood to the brain. It is contemplated that when the procedure is completed, the insertion steps may be performed in reverse to remove the system 400.

Figure 4:
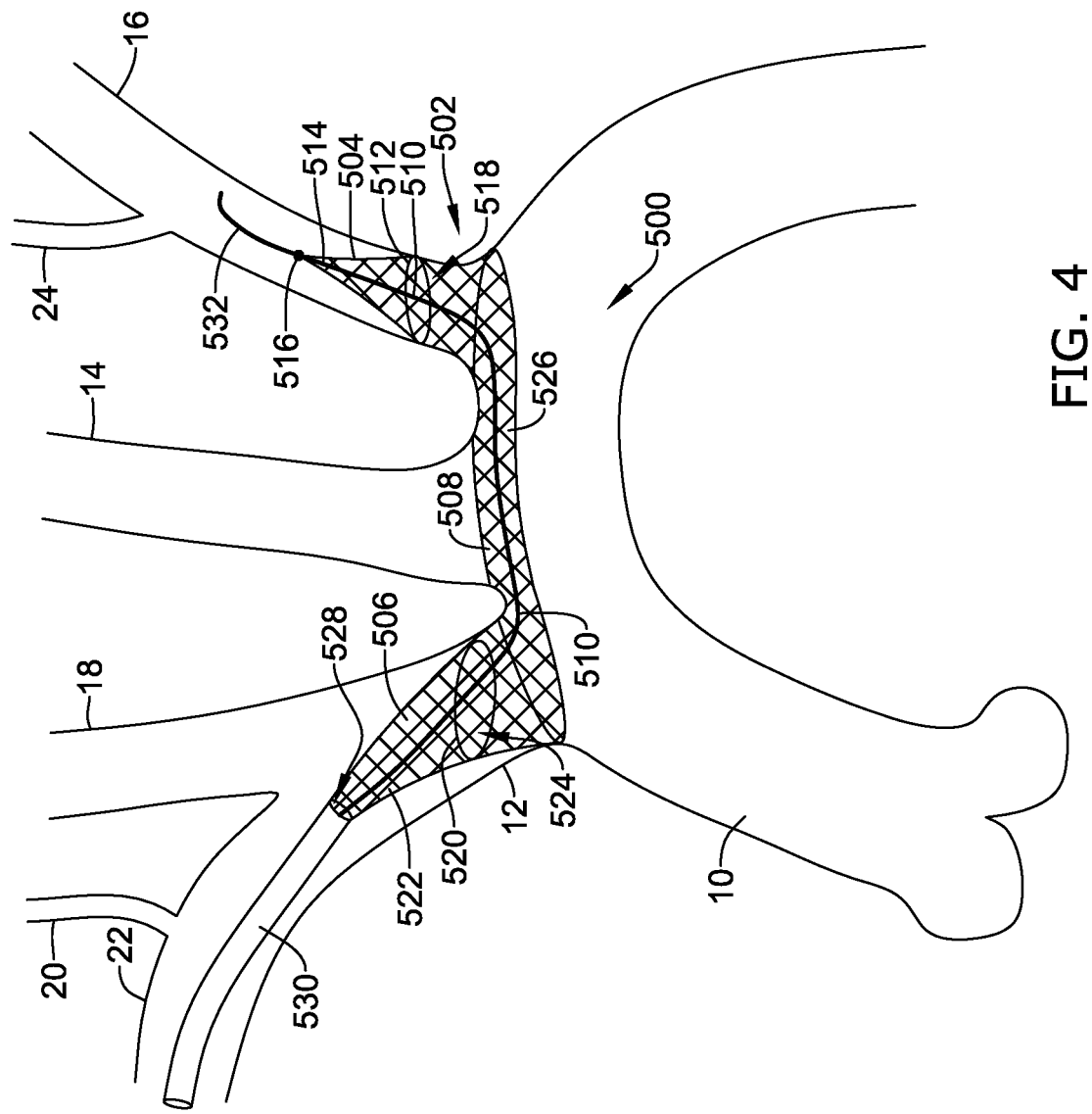
FIG. 4 illustrates a dual filter system including a deflector.

FIG. 4 illustrates another illustrative protection device 500, or filter system in which a single filter assembly 502 is configured to protect all four cerebral arteries 14, 18, 20, 24. The filter assembly 502 may include a distal filter 504, a proximal filter 506, a deflector 508, and a filter wire 510. The distal filter 504 and the proximal filter 506 may be linked by the deflector 508. In some embodiments, the distal filter 504 may be configured to be positioned in the left subclavian artery 16, the proximal filter 506 may be configured to be positioned in the innominate artery 12, and the deflector 508 may be positioned across the ostium of the left common carotid artery 14. However, other configurations are also contemplated. In other instances, the distal filter 504 may be positioned in the left common carotid artery 14, the proximal filter 506 may positioned in the innominate artery 12, and the deflector 508 over the ostium of the left subclavian artery 16. In another example, the distal filter 504 may be positioned in the left subclavian artery 16, the proximal filter 506 may positioned in the left common carotid artery 14, and the deflector 508 over the ostium of the innominate artery 12.

The distal filter 504 may include an expandable frame 512 (which may be similar in form and function to the support members 31, 35 described herein), a porous filter material 514 (which may be similar in form and function to the filter elements 33, 37 described herein), and one or more filter wires 510. In some embodiments, the filter wire 510 may be coupled to a distal end 516 of the distal filter 504, although this is not required. The filter wire 510 may be coupled to the distal filter 504 at any location desired. As shown in FIG. 4, the distal filter 504 has a generally proximally-facing opening 518. In other embodiments, the opening 518 may be distally facing. The orientation of the opening 518 may vary depending on where the access incision is located and/or the vessel in which it is deployed.

The proximal filter 506 may include an expandable frame 520 (which may be similar in form and function to the support members 31, 35 described herein), a porous filter material 522 (which may be similar in form and function to the filter elements 33, 37 described herein), and one or more filter wires 510. In some embodiments, the filter wire 510 may not be coupled to the proximal filter 506, while in other embodiments, the filter wire 510 may be coupled to the proximal filter 506 at any location desired. As shown in FIG. 4, proximal filter 506 has a generally distally-facing opening 524. In other embodiments, the opening 524 may be proximally facing. The orientation of the opening 518 may vary depending on where the access incision is located and/or the vessel in which it is deployed.

The deflector 508 may include a porous filter material 526 (which may be similar in form and function to the filter elements 33, 37 described herein). The filter material 526 may be coupled to and extend between the distal filter 504 and the proximal filter 506. It is contemplated that the positioning of the distal filter 504 and the proximal filter 506 may position the deflector 508 over the ostium of the left common carotid artery 14. However, the deflector 508 may be provided with an expandable frame (not explicitly shown) to facilitate positioning and/or deployment of the deflector 508.

The filter wire 510 may be used to help position and/or maintain the distal filter 504 at the desired target location. The filter wire 510 may be configured to extend through a lumen 528 of a catheter or delivery sheath 530 to a point outside the body where the filter wire 510 can be manipulated by a user. In some embodiments, the filter assembly 502 may also include one or more pull wires which may be actuated to exert a force on one or both of the frames 512, 520 to help position and/or conform the filter assembly 502 to the upper curve of the aortic arch 10. In this manner, not only are all cerebral arteries 14, 18, 20, 24 protected but the filter assembly 502 may not interfere with medical devices, catheters, etc., being passed through the aortic arch 10.

The lumen 528 of the delivery sheath 530 may be configured to receive other medical devices, including, but not limited to an angiography or pigtail catheter, a TAVR procedural catheter (or another procedural catheter or device), etc. The entire filter assembly 502 (e.g., the distal filter 504, proximal filter 506, deflector 508, and filter wire 510) may be loaded within the delivery sheath 530 for delivery to the target location. In some embodiments, the delivery sheath 530 may have a diameter large enough for a procedural catheter to pass therethrough, although this is not required. The delivery sheath 530 may comprise an atraumatic distal tip. The protection device 500 and other protection devices described herein may be flexible and/or atraumatic. The delivery sheath 530 may comprise a curvature, for example based on an intended placement location (e.g., the innominate artery 12 and/or the left subclavian artery 16). While not explicitly shown, a handle may be coupled to a proximal end region of the protection system 500 and may be articulated to facilitate deployment of the filter assembly 502 and/or navigation of the delivery sheath 530.

The system 500 is advanced into and through the subject's right radial artery or right brachial artery. The system 500 may be advanced over or in conjunction with one or more guidewires 532. The delivery sheath 530 may be advanced through the innominate artery 12 and into the aortic arch 10. The delivery sheath 530 may be further advanced to cannulate the left subclavian artery 16. The delivery sheath 530 may be curved and/or steerable to facilitate navigation from the right radial artery or right brachial artery to the left subclavian artery 16. During navigation, the filter assembly 502 may be held in a collapsed configuration within the lumen 528 of the delivery sheath 530. When the outer sheath 530 is at or adjacent to the target deployment region, the outer sheath 530 may then be proximally withdrawn to deploy the distal filter 504 in the left subclavian artery 16. It is contemplated that the user may grasp a proximal end of the filter wire 510 to maintain the distal filter 504 in the desired configuration as the delivery sheath 530 is withdrawn. As the delivery sheath 530 is further withdrawn, the deflector 508 is exposed and deployed across the ostia of the left common carotid artery 14. Continued proximal retraction of the delivery sheath 530 deploys the proximal filter 506 in the innominate artery 12.

As can be seen in FIG. 4, the protection system 500 traps (and/or deflects) foreign particles and prevents them from traveling into the four arteries 14, 18, 20, 24 that carry oxygenated blood to the brain. It is contemplated that when the procedure is completed, the insertion steps may be performed in reverse to remove the system 500.

Figure 5:
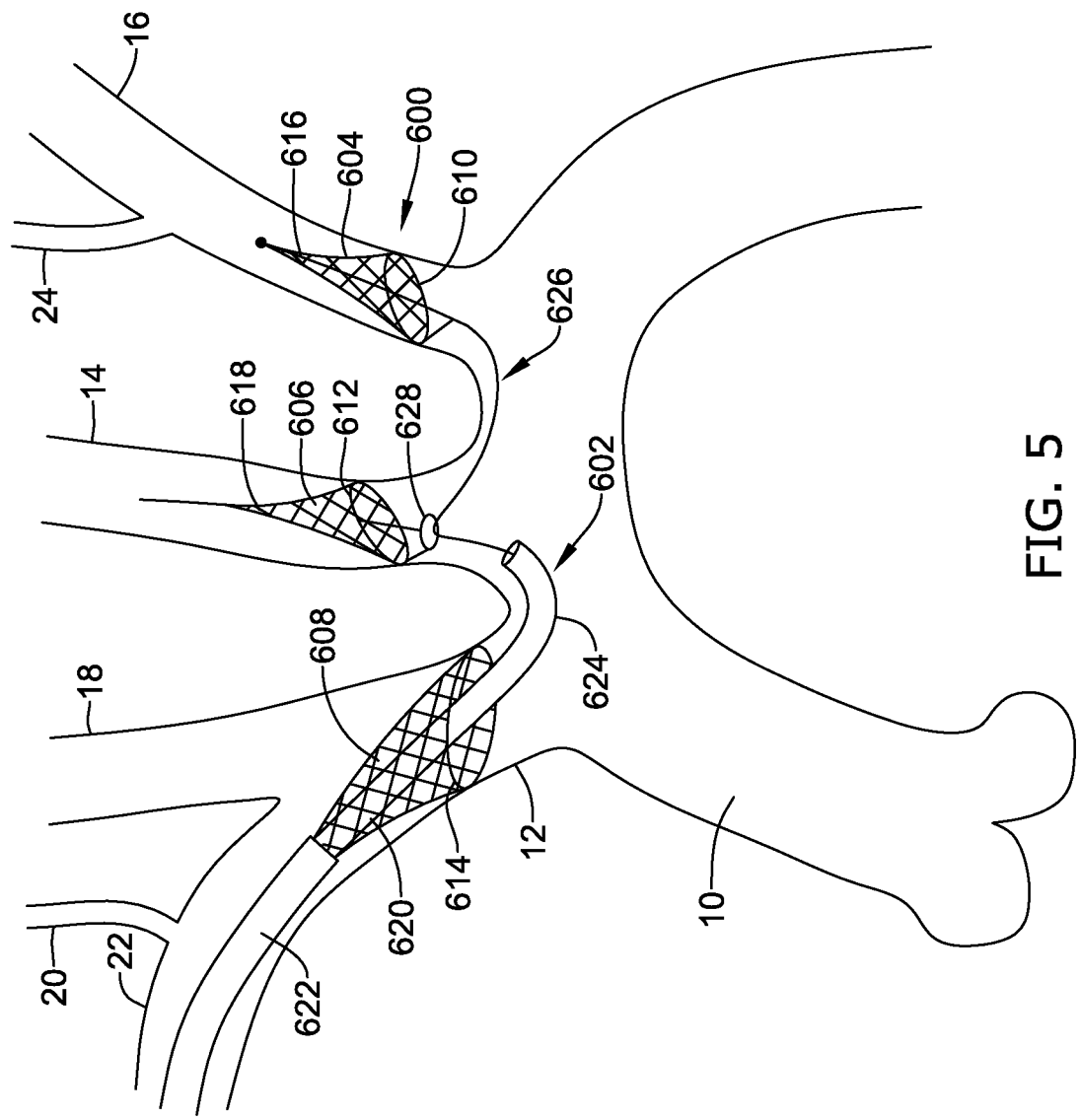
FIG. 5 illustrates another embodiment of a three filter system.

FIG. 5 illustrates another illustrative protection device, or filter system, 600 in which three filters are delivered with a single delivery device. The filter system 600 may include a distal end region 602 including at least a first filter assembly 604, a second filter assembly 606, and a third filter assembly 608 and a proximal end region (not explicitly shown) coupled to a handle (not explicitly shown) configured to remain outside the body. The first filter assembly 604, second filter assembly 606, and third filter assembly 608 may each include a support member or frame 610, 612, 614 and a filter element 616, 618, 620. The support members 610, 612, 614 may be similar in form and function to the support members 31, 35 described herein. The filter elements 616, 618, 620 may be similar in form and function to the filter elements 33, 37 described herein. In some cases, the handle of the filter system 600 may be similar in form and function to the handle 40 described herein.

The distal end region 602 may include a proximal sheath 622, a proximal shaft (not explicitly shown) similar in form and function to the proximal shaft 54 described with respect to FIG. 1A coupled to the expandable proximal, or third, filter assembly 608, a distal shaft (not explicitly shown) similar in form and function to the distal shaft 56 described with respect to FIG. 1A coupled to a distal articulatable sheath 624, the intermediate, or second, filter assembly 606, the distal, or first filter assembly 604, and a guiding member (not explicitly shown). In the filter system 600 illustrated in FIG. 5, both the first filter assembly 604 and the second filter assembly 606 may be loaded into the distal sheath 624 for delivery while the third filter assembly is loaded into the proximal sheath 622 for delivery. The first and second filter assemblies 604, 606 may be coupled together via a wire or tether 626. In some cases, the tether 626 may be made having a predetermined shape to better assist the tether 626 in seating and spanning the distance from the ostium of the left subclavian artery 16 to the left common carotid artery 14.

The system 600 is advanced into the subject's right radial artery through an incision in the right arm, or alternatively through the right brachial artery. While not explicitly shown, the system 600 may be advanced over or in conjunction with one or more guidewires. The system is advanced through the right subclavian artery 22 and into the innominate artery 12, and a portion of the system is positioned within aortic arch 10. The proximal sheath 622 is retracted proximally to allow proximal filter support element 614 to expand to an expanded configuration against the wall of the innominate artery 12, as is shown in FIG. 5. The proximal filter element 620 is secured either directly or indirectly to support element 614 and is therefore reconfigured to the configuration shown in FIG. 5. The position of distal sheath 624 can be substantially maintained while proximal sheath is retracted proximally. Once expanded, the proximal filter assembly 608 filters blood traveling through the innominate artery 12, and therefore filters blood traveling into the right common carotid artery 18 and the right vertebral artery 20. The expanded proximal filter assembly 608 is therefore in position to prevent foreign particles from traveling into the right common carotid artery 18 and the right vertebral artery 20 and into the cerebral vasculature.

The distal sheath 624 is then steered, or bent, and the distal end of the distal sheath 624 is advanced into the left subclavian artery 16. The guiding member (not explicitly shown) is thereafter advanced distally relative to distal sheath 624, allowing the distal support element 610 to expand from a collapsed configuration to a deployed configuration against the wall of the left subclavian artery 16, as shown in FIG. 5. Alternatively, or additionally, the distal sheath 624 may be proximally retracted to deploy the distal filter assembly 604. The distal filter element 616 is also reconfigured into the configuration shown in FIG. 5. Once expanded, the distal filter assembly 604 filters blood traveling through the left subclavian artery 16. The expanded distal filter assembly 604 is therefore in positioned to prevent foreign particles from traveling into the left subclavian artery 16 and the left vertebral artery 24 and into the cerebral vasculature.

Once the distal filter assembly 604 has been positioned in the left subclavian artery, the tether 626 may be distally advanced to provide additional length or "slack" to allow the distal sheath 624 to be repositioned. In some embodiments, the tether 626 may pass through an eyelet 628 which is coupled to the second filter 606. The distal sheath 624 may be manipulated to then cannulate the left common carotid artery 14. The guiding member (not explicitly shown) is thereafter advanced distally relative to distal sheath 624, allowing the intermediate support element 612 to expand from a collapsed configuration to a deployed configuration against the wall of the left common carotid artery 14, as shown in FIG. 5. The intermediate filter element 618 is also reconfigured into the configuration shown in FIG. 5. Once expanded, the intermediate filter assembly 606 filters blood traveling through the left common carotid artery 14. In some embodiments, the distal filter assembly 604 and the intermediate filter assembly 606 may be deployed prior to the deployment of the proximal filter assembly 608. The intermediate filter assembly 606 is therefore in position to trap foreign particles and prevent them from traveling into the cerebral vasculature. As can be seen in FIG. 5, the protection system 600 traps foreign particles and prevent them from traveling into the four arteries 14, 18, 20, 24 that carry oxygenated blood to the brain. It is contemplated that when the procedure is completed, the insertion steps may be performed in reverse to remove the system 600.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding filter" include "instructing deployment of a self-expanding filter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For example, "substantially straight" includes "straight."

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of inhibiting embolic material from entering cerebral vasculature, the method comprising:
    deploying a first filter system by positioning a guidewire through a right subclavian artery and into a left common carotid artery;
    tracking a distal portion of the first filter system over the guidewire, the distal portion of the first filter system comprising a proximal self-expanding filter assembly including a proximal filter and a distal self-expanding filter assembly including a distal filter;
    deploying the proximal filter in an innominate artery;
    steering the distal self-expanding filter assembly into the left common carotid artery;
    deploying the distal filter in the left common carotid artery;
    prior to, simultaneously with, or after deploying the first filter system, deploying a second filter system by tracking a distal portion of the second filter system into a left subclavian artery, the distal portion of the second filter system comprising:
        an outer sheath;
        an inner tubular member within the outer sheath; and
        an additional self-expanding filter assembly within the outer sheath and coupled to the inner tubular member; and
    at least one of proximally retracting the outer sheath and distally advancing the inner tubular member to deploy the additional self-expanding filter assembly from the outer sheath;
    wherein the second filter system further comprises a catheter disposed within the inner tubular member, a distal end region of the catheter having an arcuate shape, wherein after tracking the distal portion of the second filter system into the left subclavian artery, the method further comprises advancing the catheter distally from the inner tubular member into an aortic arch or ascending aorta;
    wherein the distal end region of the catheter includes a plurality of apertures in fluid communication with a lumen of the catheter, wherein the method further comprises delivering contrast media through the catheter.

2. The method of claim 1, wherein deploying the second filter system includes tracking the distal portion of the second filter system from an incision in a left brachial artery or left radial artery into the left subclavian artery.

3. The method of claim 1, wherein deploying the second filter system includes tracking the distal portion of the second filter system from an incision in a femoral artery into the left subclavian artery.

4. The method of claim 1, wherein no part of the first and second filter systems are connected to each other.

5. The method of claim 1, wherein an opening of the additional self-expanding filter assembly is positioned in the left subclavian artery, upstream of a left vertebral artery.

6. The method of claim 5, wherein the opening is a distally facing opening.

7. The method of claim 1, wherein an opening of the additional self-expanding filter assembly is positioned in an aortic arch, upstream of the left subclavian artery.

8. The method of claim 1, wherein an opening of the additional self-expanding filter assembly is positioned in a left vertebral artery.

9. The method of claim 1, wherein the additional self-expanding filter assembly is deployed from the outer sheath after delivering contrast media.

10. The method of claim 9, wherein after deploying the additional self-expanding filter assembly, withdrawing the catheter.

11. The method of claim 1, further comprising performing an endovascular procedure, wherein the deployed proximal and distal filters of the first filter system, and the additional self-expanding filter assembly of the second filter system all inhibiting embolic material from entering cerebral vasculature through the right subclavian artery, a right vertebral artery, a right carotid artery, a left carotid artery, the left subclavian artery, and a left vertebral artery during the endovascular procedure.

12. The method of claim 11, further comprising after performing the endovascular procedure, withdrawing the proximal and distal filter assemblies of the first filter system, and the additional self-expanding filter assembly of the second filter system.

13. A method of inhibiting embolic material from entering cerebral vasculature, the method comprising:
    deploying a first filter system by positioning a guidewire through a right subclavian artery and into a left common carotid artery;

tracking a distal portion of a first protection device over the guidewire, the distal portion of the first protection device comprising:
  a proximal sheath;
  a proximal self-expanding filter assembly within the proximal sheath;
  a distal sheath; and
  a distal self-expanding filter assembly within the distal sheath;
at least one of proximally retracting the proximal sheath and distally advancing the proximal self-expanding filter assembly to deploy the proximal self-expanding filter assembly from the proximal sheath in an innominate artery;
steering the distal sheath into the left common carotid artery;
at least one of proximally retracting the distal sheath and distally advancing the distal self-expanding filter assembly to deploy the distal self-expanding filter assembly from the distal sheath in the left common carotid artery;
after deploying the proximal and distal self-expanding filter assemblies, withdrawing the proximal and distal sheaths;
prior to, simultaneously with, or after deploying the first filter system, deploying a second filter system by tracking a distal portion of a second protection device into a left subclavian artery, the distal portion of the second protection device comprising:
  an outer sheath;
  an inner tubular member within the outer sheath; and
  an additional self-expanding filter assembly within the outer sheath and coupled to the inner tubular member; and
at least one of proximally retracting the outer sheath and distally advancing the inner tubular member to deploy the additional self-expanding filter assembly from the outer sheath;
wherein the second filter system further comprises a catheter disposed within the inner tubular member, a distal end region of the catheter having an arcuate shape, wherein after tracking the distal portion of the second filter system into the left subclavian artery, the method further comprises advancing the catheter distally from the inner tubular member into an aortic arch or ascending aorta;
wherein the distal end region of the catheter includes a plurality of apertures in fluid communication with a lumen of the catheter, wherein the method further comprises delivering contrast media through the catheter.

14. The method of claim 13, wherein deploying the second filter system includes tracking the distal portion of the second protection device from an incision in a left brachial artery or left radial artery into the left subclavian artery.

15. The method of claim 13, wherein no part of the first and second filter systems are connected to each other.

16. The method of claim 13, wherein an opening of the additional self-expanding filter assembly is positioned in the left subclavian artery, upstream of a left vertebral artery, wherein the opening is a distally facing opening.

17. The method of claim 13, further comprising performing an endovascular procedure, wherein the deployed proximal and distal filters self-expanding filter assemblies of the first filter system, and the additional self-expanding filter assembly of the second filter system all inhibiting embolic material from entering cerebral vasculature through the right subclavian artery, a right vertebral artery, a right carotid artery, a left carotid artery, the left subclavian artery, and a left vertebral artery during the endovascular procedure, the method further comprising after performing the endovascular procedure, withdrawing the proximal and distal self-expanding filter assemblies of the first filter system, and the additional self-expanding filter assembly of the second filter system.

* * * * *